(12) United States Patent
Hsieh et al.

(10) Patent No.: US 12,308,108 B2
(45) Date of Patent: May 20, 2025

(54) AUTOMATICALLY DETECTING CHARACTERISTICS OF A MEDICAL IMAGE SERIES

(71) Applicant: GE Precision Healthcare LLC, Milwaukee, WI (US)

(72) Inventors: Jiang Hsieh, Brookfield, WI (US); Maud Bonnard, Brookfield, WI (US); Sandeep Dutta, Kissimmee, FL (US)

(73) Assignee: GE Precision Healthcare LLC, Waukesha, WI (US)

( * ) Notice: Subject to any disclaimer, the term of this patent is extended or adjusted under 35 U.S.C. 154(b) by 495 days.

(21) Appl. No.: 17/407,516

(22) Filed: Aug. 20, 2021

(65) Prior Publication Data

US 2023/0056923 A1 Feb. 23, 2023

(51) Int. Cl.
*G06T 7/00* (2017.01)
*G06V 10/82* (2022.01)
*G16H 30/20* (2018.01)
*G16H 30/40* (2018.01)
*G16H 40/20* (2018.01)

(52) U.S. Cl.
CPC ........... *G16H 30/40* (2018.01); *G06T 7/0012* (2013.01); *G06V 10/82* (2022.01); *G16H 30/20* (2018.01); *G16H 40/20* (2018.01)

(58) Field of Classification Search
CPC ........ G16H 30/40; G16H 30/20; G16H 40/20; G16H 15/00; G16H 50/20; G06T 7/0012; G06V 10/82
See application file for complete search history.

(56) References Cited

U.S. PATENT DOCUMENTS 8,160,322 B2   4/2012  Dikmen et al.
11,238,974 B2 *  2/2022  Yokokubo .............. G16H 30/20
(Continued)

OTHER PUBLICATIONS

Criminisi, A. et al. | Anatomy Detection and Localization in 3D Medical Images. In: Criminisi A., Shotton J. (eds) DecisionForests for Computer Vision and Medical Image Analysis. Advances in Computer Vision and Pattern Recognition. 2013, Springer, London, pp. 193-209.
(Continued)

*Primary Examiner* — Ming Y Hon
(74) *Attorney, Agent, or Firm* — Amin, Turocy & Watson, LLP

(57) ABSTRACT

Techniques are described for automatically detecting scan characteristics of a medical image series. According to an embodiment, a system is provided that comprises a memory that stores computer executable components, and a processor that executes the computer executable components stored in the memory. The computer executable components comprise an image generation component that generates a representative image of a medical image series comprising a plurality of scan images, and a series characterization component that processes the representative image using one or more characteristic detection algorithms to determine one or more characteristics of the medical image series. The system can further tailor the visualization layout for viewing the medical image series based on the one or more characteristics and/or automatically perform various workflow tasks based on the one or more characteristics.

22 Claims, 12 Drawing Sheets

(56) References Cited

U.S. PATENT DOCUMENTS

| | | | | |
|---|---|---|---|---|
| 11,759,165 | B2* | 9/2023 | Takada | A61B 8/5207 600/443 |
| 2012/0183188 | A1* | 7/2012 | Moriya | G16H 30/20 382/128 |
| 2014/0143719 | A1* | 5/2014 | Arazi | G16H 30/20 715/810 |
| 2015/0363053 | A1* | 12/2015 | Aoyama | G16H 30/40 715/838 |
| 2016/0292155 | A1* | 10/2016 | Adriaensens | G16H 30/20 |
| 2017/0300664 | A1* | 10/2017 | Matsuki | G16H 30/20 |
| 2019/0197135 | A1* | 6/2019 | Beymer | G16H 50/70 |
| 2019/0197418 | A1* | 6/2019 | Abutbul | G06F 9/54 |
| 2020/0085382 | A1* | 3/2020 | Taerum | G06T 7/0016 |
| 2020/0152316 | A1* | 5/2020 | Lee | G06N 20/00 |
| 2020/0178839 | A1* | 6/2020 | Krishnaiyer Raman | G01R 33/283 |
| 2020/0211692 | A1* | 7/2020 | Kalafut | G06N 20/00 |
| 2020/0219262 | A1* | 7/2020 | Hsiao | G06V 10/764 |
| 2020/0311937 | A1* | 10/2020 | Wang | G06T 7/11 |
| 2020/0380675 | A1* | 12/2020 | Golden | G06T 7/143 |
| 2021/0041517 | A1* | 2/2021 | Borisch | A61B 6/032 |
| 2021/0073977 | A1* | 3/2021 | Carter | G06T 11/20 |
| 2021/0278939 | A1* | 9/2021 | Miyamoto | G16H 10/60 |
| 2021/0390679 | A1* | 12/2021 | Lee | G06V 10/82 |
| 2022/0005258 | A1* | 1/2022 | Mory | A61B 6/5223 |
| 2022/0051400 | A1* | 2/2022 | Izadyyazdanabadi | G06T 11/001 |
| 2022/0051771 | A1* | 2/2022 | Lyman | G06T 7/0014 |
| 2022/0215961 | A1* | 7/2022 | Jacobs | G16H 50/70 |
| 2022/0319153 | A1* | 10/2022 | Iwaki | G06T 7/11 |
| 2023/0033122 | A1* | 2/2023 | Muhsin | G16H 40/40 |
| 2023/0352147 | A1* | 11/2023 | Abdolell | A61B 8/582 |

OTHER PUBLICATIONS

Ruiz P. | Understanding and visualizing ResNets. Webpage https://towardsdatascience.com/understanding-and-visualizing-resnets-442284831be8, last accessed on Jul. 1, 2021, 8 pages.

* cited by examiner

AUTOMATICALLY DETECTING CHARACTERISTICS OF A MEDICAL IMAGE SERIES

TECHNICAL FIELD

This application relates to automatically detecting the characteristics of a medical image series.

BACKGROUND

The healthcare industry has innumerable opportunities to leverage artificial intelligence (AI), machine learning (ML), and other analytical models to achieve more accurate, proactive, and comprehensive patient care. From reducing administrative burdens to supporting precision medicine, these analytical tools are showing promise across clinical, financial, and operational domains. Learning algorithms, for instance, can become more precise and accurate as they interact with training data, allowing humans to gain unprecedented insights into diagnostics, care processes, treatment variability, and patient outcomes. However, even organizations with industry-leading analytics competencies in hand are facing complex challenges when it comes to applying various analytics to clinical care.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are provided that facilitate automatically detecting scan characteristics of a medical image series.

According to an embodiment, a system is provided that comprises a memory that stores computer executable components, and a processor that executes the computer executable components stored in the memory. The computer executable components comprise an image generation component that generates a representative image of a medical image series comprising a plurality of scan images. In particular, the medical image series can include two-dimensional (2D) anatomy scans generated from three-dimensional (3D) medical imaging scan data representative of a three-dimensional (3D) volume of an anatomical region of a patient, such as that generated using a computed tomography (CT) scan, a magnetic resonance imaging (MRI) scan, or another 3D medical imaging scanning modality. The image generation component generates the representative image from the 3D data using a novel to 2D image compression processes.

The computer executable components further comprise a series characterization component that processes the representative image using one or more characteristic detection algorithms to determine one or more characteristics of the medical image series. The more characteristic detection algorithms can include but are not limited to, a scan type detection algorithm, an anatomic region detection algorithm, a contrast phase detection algorithm, and a foreign object detection algorithm. In this regard, the one or more scan characteristics can include, but are not limited to, the type of the scan, the anatomical region or regions scanned, the iodinated contrast phase represented, and presence/absence of foreign objects (e.g., metal implants/devices).

In various embodiments, the one or more characteristic detection algorithms comprise a series of detection algorithms applied to the representative image in series and the scan characterization component selects subsequent detection algorithms in the series based on results of preceding detection algorithms in the series. For example, the one or more characteristics detection algorithms can comprise a first detection algorithm and a second detection algorithm, and wherein the scan characterization component selects the second detection algorithm from amongst a plurality of second detection algorithms based on the results of the first detection algorithm. In one or more embodiments, the first detection algorithm comprises a scan type detection algorithm adapted to detect a type of the medical image series wherein the second detection algorithms are tailored to different types of medical image series.

The system can further tailor the visualization layout for viewing the medical image series based on the one or more characteristics and/or automatically perform various workflow tasks based on the one or more characteristics. For example, based on the detected characteristics of the medical image series, the system can automatically call and apply appropriate medical image processing workflows to the medical image series, find and pull related cases for the same patient for longitudinal study analysis, find and pull related cases for different patients for comparative analysis, and the like.

In some embodiments, elements described in the disclosed systems can be embodied in different forms such as a computer-implemented method, a computer program product, or another form.

DETAILED DESCRIPTION

Figure 1:
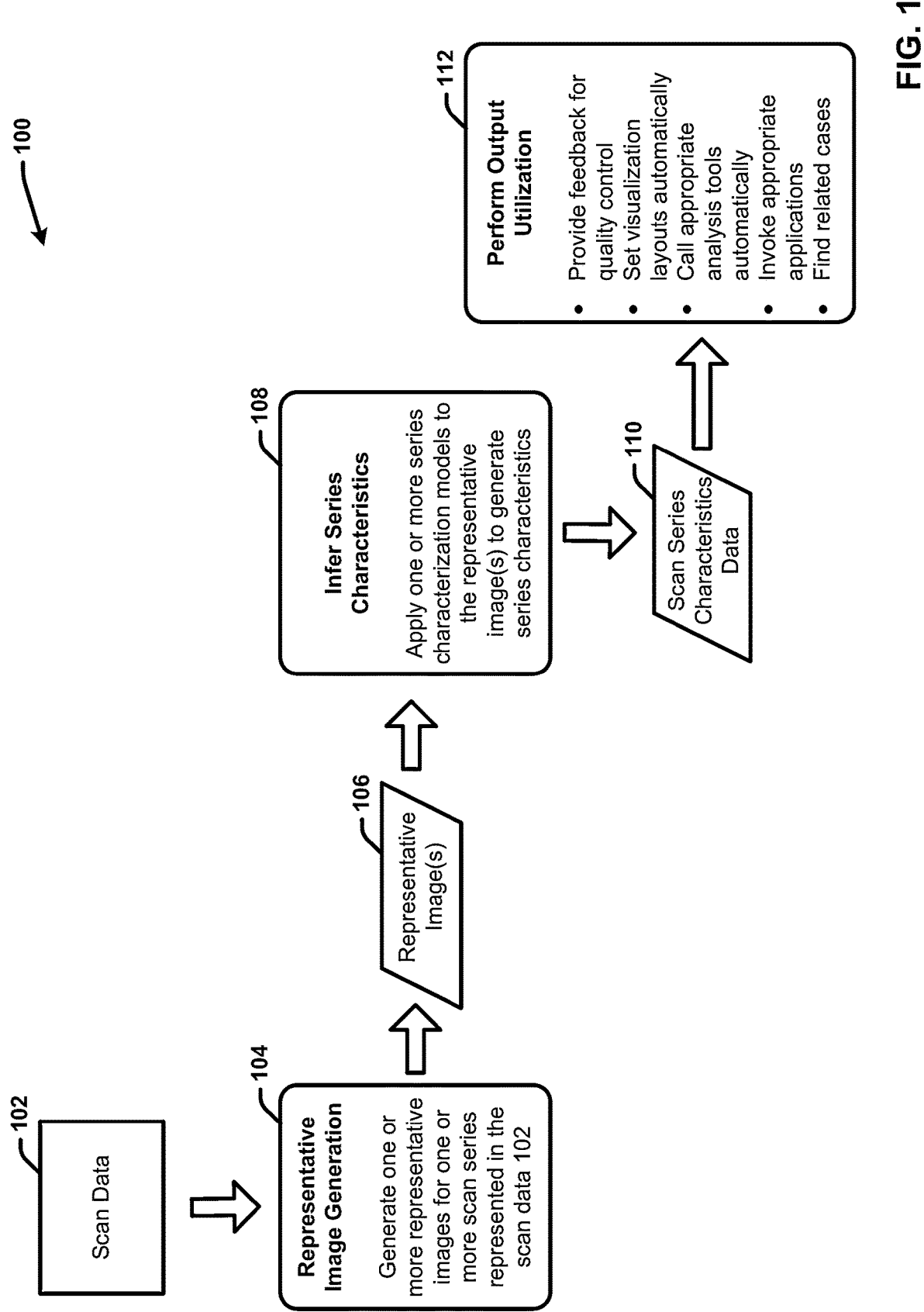
FIG. 1 illustrates a high-level flow diagram of an example computer implemented process for automatically detecting scan characteristics of a medical image series for workflow automation in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate automatically detecting scan characteristics of a medical image series for workflow automation. The disclosed techniques propose an optimized single image representation of a medical image series (e.g., a CT image series). The representative images are used to train one or more intelligent algorithm (e.g., deep learning networks) to automatically detect specific exam characteristics of that image series. The characteristics can include (but are not limited to): the type of the series/exam; the anatomic region was scanned; the iodinated contrast phase present in the series images; and the presence or absence of metal implants/devices.

The goal of the disclosed techniques is to simplify the subsequent workflow steps (e.g., in trauma workflows and other) in an exam where multiple image series are present. Today it is a manual process for technologists and clinicians to determine what each image series represents and then set up the visualization layouts, post-processing steps, and analysis tools for each series. This invention aims to significantly automate the process. In this regard, one of the drawbacks of medical imaging systems today is the image series description tags are not consistently filled in accurately or compliantly in the field (e.g., in the Digital Imaging and Communications in Medicine (DICOM) format or another format). For example, series descriptions vary between sites/regions, and are editable by the technicians at time of scan if necessary. In addition, scan ranges and injection protocols vary depending on exams and patients and these parameters are often not recorded by the technician or the imaging system at the time of the scan. This is particularly the case in acute care settings such as emergency room (ER) settings and similar time/resource constrained settings. In such settings, even the scan protocols that are used may be those that were set up for a different patient or purpose then needed for the current patient and use-case. Thus, there is no guarantee that what the series description and tags indicate provided accurately depict the correct contents of the image series.

The disclosed systems and methods overcome these challenges by providing a technique wherein an entire image series can be represented as a single representative image. One or more machine learning (e.g., deep learning or the like) series characterization algorithms (or models) are then used to classify the representative image into various categories. In addition, multiple models, each for a specific task of characterization, can be applied in sequence to provide multiple levels of information that can be used in the final use-case. For example, an anatomy detection model can be used to select which contrast phase detection model (e.g., specific for an anatomic region) should be run. Similarly, this can next be used to select and run an artifact detection model for that anatomy. The models can also be used in conjunction with DICOM tags for reconstruction parameters and relevant patient information (e.g., demographic information, medical history information, etc.) to facilitate automating the analysis and workflow even further.

For example, in various embodiments, based on the automatically detected scan characteristics, the disclosed system can automatically optimize the visualization layout presented to clinicians for reviewing the scan images. This is a game changer in trauma and oncology scans that require a significant number of series to review with variable protocols, significantly reducing the amount of manual intervention needed today from technicians and clinicians. For example, in the trauma workflow, where the exams often contain multiple series of different anatomy regions in the body (sometimes up to a dozen), the visualization layouts for each series can be set up automatically with the correct display settings. In addition, the appropriate tools for an anatomy or type of scan can be made available for only that window where that series is displayed.

The automatically detected scan characteristics can also be used to automatically invoke the appropriate post-processing applications. For example, automated algorithms and analysis can be run for each series without needing the clinician to manually invoke them. For instance, in one example use-case for an automated cardiac exam, the exam type detection can determine which series is the most appropriate for calcium scoring analysis and which is for the coronary analysis. The analysis steps for each can be automatically invoked and reports generated. Similarly knowing the content of each series, even specific heart chamber segmentation algorithms or other image processing algorithms (e.g., organ segmentation, fat segmentation, lesion detection/scoring, and the like) can be invoked automatically and added to the report.

In various embodiments, the medical image series/exams include CT scans, including multi-energy CT images and material images for dual energy CT and spectral CT. However, the disclosed techniques can be applied to other 3D medical imaging modalities, including but not limited to, MRI, positron emission tomography (PET), ultrasound, and the like. The disclosed techniques are further anatomy and acquisition protocol (e.g., contrast/non-contrast) agnostic.

In this regard, the types of medical images processed/analyzed using the techniques described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MR) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MR capture modality, a US capture modality, a CD capture modality, a PET capture modality, a SPECT capture modality, a NM capture modality, and the like.

The term "multiphase" as used herein with respect to medical imaging refers to capture of image data of the same patient/anatomy using a same capture modality yet under different conditions. In various embodiments, the different conditions can include different acquisition protocols, different acquisition prescription planes (e.g., capture orientation), and/or different physiological phases. The resulting image data can include different sets or series of medical images captured in association with each of the different phases.

In various embodiments, the different physiological phases can be based on contrast injection. For example, the dual vascular supply of liver (75% portal venous and 25% hepatic arterial) results in sequential opacification of hepatic arteries, portal veins, and hepatic veins after injection of intravenous contrast. Different tissues and structures reach peak enhancement at different times. This allows the acquisition of images during different time ranges or "dynamic phases" to highlight these differences. In this regard, multiphase MR and/or multiphase CT can refer to image acquisition at sequential time ranges before and after contrast administration. While these phases are a continuum, they are described as distinct time ranges for simplicity and clinical utility. In some embodiments, multiphase MR and/or multiphase CT can include image data captured two or more of the following phases: pre-contrast phase (or unenhanced phase), intravenous (IV) phase (IVP), arterial phase (AP), early AP, late AP, extracellular phase (ECP), portal venous phase (PVP), delayed phase (DP), transitional phase (TP), hepatobiliary phase (HBP), and variants thereof.

As used herein, a "3D image" refers to digital image data representing an object, space, scene, and the like in three dimensions, which may or may not be displayed on an interface. 3D images described herein can include data representing positions, geometric shapes, curved surfaces, and the like. In an aspect, a computing device, such as a graphic processing unit (GPU) can generate a 3D image based on the data, performable/viewable content in three dimensions. For example, a 3D image can include a collection of points represented by 3D coordinates, such as points in a 3D Euclidean space (e.g., a point cloud). The collection of points can be associated with each other (e.g., connected) by geometric entities. For example, a mesh comprising a series of triangles, lines, curved surfaces (e.g. non-uniform rational basis splines ("NURBS")), quads, n-grams, or other geometric shapes can connect the collection of points. In an aspect, portions of the mesh can include image data describing texture, color, intensity, and the like.

A 3D anatomy image refers to a 3D or volumetric representation of an anatomical region of a patient. In some implementations, a 3D anatomy image can be captured in 3D directly by the acquisition device and protocol. In other implementations, a 3D anatomy image can comprise a generated image that was generated from one-dimensional (1D) two-dimensional (2D) and/or 3D sensory and/or image data captured of the anatomical region of the patient. Some example 3D medical images include 3D volume images generated from CT scan data, and MRI scan data. It is noted that the terms "3D image," "3D volume image," "volume image," "3D model," "3D object,", "3D reconstruction," "3D representation," "3D rendering," and the like are employed interchangeably throughout, unless context warrants particular distinctions among the terms. It should be appreciated that such terms can refer to data representing an object, an anatomical region of the body, a space, a scene, and the like in three dimensions, which may or may not be displayed on an interface. The terms "3D data," and "3D image data" can refer to a 3D image itself, data utilized to generate a 3D image, data describing a 3D image, data describing perspectives or points of view of a 3D image, capture data (e.g., sensory data, images, etc.), meta-data associated with a 3D image, and the like. It is noted that the term "2D image" as used herein can refer to data representing an object, an anatomical region of the body, a space, a scene, and the like in two dimensions, which may or may not be displayed on an interface.

The term "3D anatomy scan data" is used herein to refer to the collection of scan data acquired/generated in association with a performance of a 3D medical imaging scan, such as a CT scan, an MRI scan, a PET scan or the like. For example, 3D anatomy scan data can include 1D, 2D and 3D data that can be used to generate a 3D volumetric image of the scanned anatomy and to generate 2D scan images corresponding to slices of the 3D volumetric image from various perspective/orientations (e.g., relative to the axial plane, the coronal plane, the sagittal plane and other reformatted views). The terms "3D anatomy scan data," "3D anatomy data," "3D scan data," and the like are used herein interchangeably unless context warrants particular distinctions amongst the terms. The term "scan slice," "image slice," "scan image," and the like are used herein interchangeably to refer to a reconstructed 2D image generated from 3D anatomy scan data that corresponds to a computer-generated cross-sectional image of an anatomical region of a patient.

The terms "thick" and "thin" as applied to a scan image/slice are used herein to refer to the relative thickness of the tissue represented in the slice, which can vary depending on the scanner detector. It should be appreciated that a thin slice has a smaller thickness than a thick slice. In accordance with most 3D medical imaging modalities (e.g., CT, MRI, PET, etc.), the native resolution of thin scan images (e.g., obtained with thin detectors) is higher than the native resolution of thicker scan images (e.g., obtained with thicker detectors). For example, the nominal slice thickness in CT is defined as the full width at half maximum (FWHM) of the sensitivity profile, in the center of the scan field; its value can be selected by the operator according to the clinical requirement and generally lies in the range between 1 millimeter (mm) and 10 mm. In general, the larger the slice thickness, the greater the low contrast resolution in the image, while the smaller the slice thickness, the greater the spatial resolution.

The term "multimodal data" is used herein to refer to two or more different types of data. The differentiation factor between the two or more different types of data can vary. For example, the differentiation factor can refer to the medium of the data (e.g., image data, text data, signal data, etc.), the format of the data, the capture modality of the data, the source of the data and so one. In the medical/clinical context, multimodal clinical refers to two or more forms of health-related information that is associated with patient care and/or part of a clinical trial program. Clinical data consist of information ranging from determinants of health and measures of health and health status to documentation of care delivery. Different types of clinical data are captured for a variety of purposes and stored in numerous databases across healthcare systems. Some example types of clinical data that may be included in a pool of multimodal clinical data from which a data cohort may be generated includes (but is not limited to): medical images and associated metadata (e.g., acquisition parameters), radiology reports, clinical laboratory data, patient electronic health record (EHR) data, patient physiological data, pharmacy information, pathology reports, hospital admission data, discharge and transfer data, discharge summaries, and progress notes.

The term "clinical inferencing model" is used herein to refer to a ML model configured to perform a clinical decision/processing on clinical data. The clinical decision/processing task can vary. For example, the clinical decision/processing tasks can include classification tasks (e.g., disease classification/diagnosis), disease progression/quantification tasks, organ segmentation tasks, anomaly detection tasks, image reconstruction tasks, and so on. The clinical inferencing models can employ various types of ML algorithms, including (but not limited to): deep learning models, neural network models, deep neural network models (DNNs), convolutional neural network models (CNNs), generative adversarial neural network models (GANs), long short-term memory models (LSTMs), attention-based models, transformers and the like. The term "multimodal clinical inferencing model" is used herein to refer to a clinical inferencing model adapted to receive and process multimodal clinical data as input. Various embodiments of the disclosed subject matter are directed to an oxygen forecasting support model that can be or include a multimodal clinical inferencing model adapted to forecast short-term oxygen support needs for patients with a respiratory condition.

As used herein, a "medical imaging inferencing model" refers to an image inferencing model that is tailored to perform an image processing/analysis task on one or more medical images. For example, the medical imaging processing/analysis task can include (but is not limited to): scan series characteristic classification, disease/condition classification, disease region segmentation, organ segmentation, disease quantification, disease/condition staging, risk prediction, temporal analysis, anomaly detection, anatomical feature characterization, medical image reconstruction, and the like. The terms "medical image inferencing model," "medical image processing model," "medical image analysis model," and the like are used herein interchangeably unless context warrants particular distinction amongst the terms.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a high-level flow diagram of an example computer implemented process 100 for automatically detecting scan characteristics of a medical image series in accordance with one or more embodiments of the disclosed subject matter.

In accordance with process 100, at 104, one or more representative images 106 are generated for one or more scan series represented in scan data 102. In this regard, the scan data 102 can include medical image series data that includes a series of 2D scan images generated in association with performance of a 3D medical imaging scan, such as a CT scan, an MRI scan, a PET scan or the like. As applied to CT, the scan images can be acquired either with single energy, dual energy, or photon counting CT. For dual energy or photon counting CT, an iodine map can be used to characterize the contrast phase of the scan. The 2D scan images may include native scan images that are generated relative to their native acquisition plane and/or reconstructed images that are regenerated from the 3D scan image volume data relative to a different acquisition plane. In some implementations, the scan data 102 may include two or more different medical image series. For example, the two or more different medical image series can correspond to different perspectives/orientations of the same anatomical region of interest (ROI) captured, different acquisition cycles, different contrast phases of a perfusion scan, and/or different ROIs. With these implementations, one or more representative images can be generated for each (or in some implementations one or more) scan series represented in the scan data 102.

In some implementations, the scan data 102 can also include or otherwise be associated with metadata describing characteristics of the medical image series associated therewith. For example, the metadata can include identifying or indicating the type of the scan, the ROI scanned, the acquisition protocols used, the scan mode used, the acquisition plane, and the scanner device/system used. The metadata can also include information regarding the reconstruction parameters used to generate the 2D scan images included in the series (e.g., reconstruction kernel size, slice thickness, the modulation transfer function (MTF) value, slice sensitivity profile (SSP), point spread function (PSF) characteristics, etc.). The metadata may also include information identifying or indicating the relative orientation of the medical image series (e.g., axial, coronal, sagittal, or another orientation) and/or the relative location/position of each (or in some implementation one or more) scan image included in the series in 3D. In some implementations in which the scan was performed with perfusion, the metadata may also include time stamp information that identifies or indicates the relative timing of capture of each scan relative to perfusion process and/or the relative phase of the perfusion process at which time each scan image was captured/generated. The metadata may also include patient information, such as information identifying or indicating (e.g., in an anonymized manner as appropriate) the identity of the patient (e.g., a unique patient identifier such a name or anonymized identification number), demographic information for the patient (e.g., age, gender, body mass index (BMI), and relevant medical history information for the patient (e.g., comorbidities, current condition/diagnosis, current pathology, reason for performance of the scan, etc.). In some embodiments, this metadata and/or patient information can be used as input in parallel and/or in combination with the one or more representative images 106 at 108 into one or more series characterization models to facilitate inferring the series characteristics, as discussed in greater detail below.

The scan data 102 can also include or otherwise be associated with 3D volume data that represents a 3D representation of the anatomical ROI captured during the 3D imaging scan. The 3D volume data can include or otherwise be associated with information that defines the relative geometry of the 3D volume and the relative position/orientation of each 2D scan image relative to the 3D volume. For example, the 3D volume data can be associated with metadata that defines the 3D bounding box of the ROI captured. In some implementations, the 3D volume data may also be associated with metadata describing the relative geometry and position of one or more anatomical features of interest reflected in the 3D volume data and/or the relative position of one or more scan planes.

The goal of the representative image generation process at 104 is to generate a single (or in some implementations two or more representative images) representative image 106 for each scan series included in the scan data 102 that captures the entire contents of the characteristics of the scan series. At a high level, the process of generating the representative image 106 can be correlated to a 3D to 2D image compression process that compresses the 3D volume image data represented by the stacked scan series images into a single 2D image that provides the most optimal representation of the entire image series for the purpose of automatically detecting defined characteristics of the scan series that may or may not be included in metadata describing the scan series. Techniques for generating the representative image 106 are discussed in greater detail infra with reference to FIG. 2 and the image generation component 210.

At 108, the representative image 106 is used to automatically infer characteristics of the series that may or may not be included in metadata describing the scan series. In this regard, as described above, many scan series may be received with no, minimal, or incorrect metadata describing relevant characteristics of the scan series, such as (but not limited to), the scan type, the anatomical ROI scanned, the contrast phase captured, and presence/absence of metal implants/devices. The disclosed techniques train deep learning models to automatically detect specific scan characteristics from the representative image(s) generated at 104. These deep learning models are referred to herein as series characterization models. In this regard, at 108, one or more series characterization models can be applied to the representative image 106 to generate scan series characteristics data 110 that provides one or more defined characteristics of each series represented in the scan data 102. The specific characteristics include in the scan series data 110 can vary depending on the type of the scan series and the available series characterization models that are applicable to the scan series. In one or more embodiments, these characteristics may include (but are not limited to), the scan type, the anatomical ROI scanned, the contrast phase depicted (if applicable), and information identifying presence/absence of metal implants/devices.

As described in greater detail infra, in various embodiments, the series characterization models that are applied to the representative image 106 can include a plurality of different models adapted to detect different characteristics. More importantly, the models can be applied in a daisy-chain fashion, wherein at least some of the models applied can be selected based on the output of one or more preceding models. For example, in some embodiments, a first model can be applied that is adapted to detect the type of the scan series. Once the scan series type has been determined, the next model that is applied can be selected from amongst a pool of different models that is specifically tailored to that scan type. The number of sequential models applied that are selected based on the output results of a preceding model can vary.

The result of the series characteristics inference process at 108 provides scan series characteristics data 110 describing the inferred (or automatically detected) characteristics of each scan series included in the scan data 102. At 112, the scan series characteristics data 110 can be employed to perform a variety of different output utilizations. For example, the scan series characteristics data 110 can be provided as feedback to the imaging system operating techniques for the purpose of quality control to ensure the correct/desired scan series characteristics were captured. This process can be performed during the scan and/or immediately upon completion of the scan while the patient remains on the scanner table so that the patient can be rescanned as needed. The system can further tailor the visualization layout for viewing the medical image series based on the one or more characteristics and/or automatically perform various workflow tasks based on the one or more characteristics. For example, based on the detected characteristics of the medical image series, the system can automatically call and apply appropriate medical image analysis tools and processing workflows to the medical image series. For instance, the analysis tools can include clinical inferencing models adapted to perform pathology detection and/or characterization, perform organ segmentation, perform image quality enhancement, and the like. The system can also invoke appropriate applications for the medical images series based on the detected series characteristics. The system can also find and pull related cases for the same patient for longitudinal study analysis, find and pull related cases for different patients for comparative analysis. Various other output utilizations are envisioned.

Figure 2:
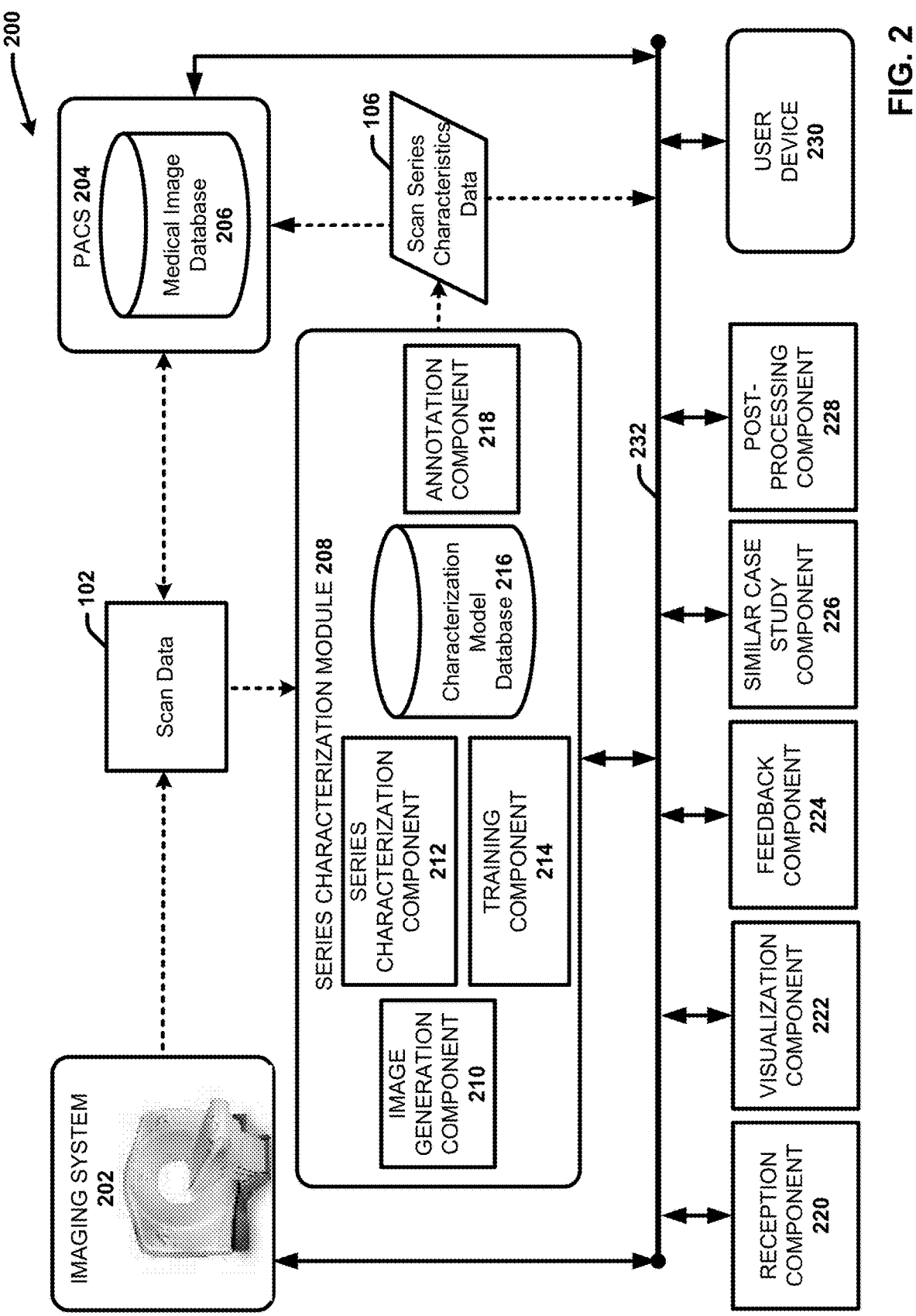
FIG. 2 illustrates a block diagram of an example, non-limiting computing system that facilitates automatically detecting scan characteristics of a medical image series in accordance with one or more embodiments of the disclosed subject matter.

FIG. 2 illustrates a block diagram of an example, non-limiting computing system 200 that facilitates automatically detecting scan characteristics of a medical image series in accordance with one or more embodiments of the disclosed subject matter. Repetitive description of like elements employed in respective embodiments is omitted for sake of brevity.

Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

In this regard, computing system 200 can be and/or include various computer executable components. In the embodiment shown, these computer executable components include series characterization module 208, reception component 220, visualization component 222, feedback component 224, similar case study component 226 and post-processing component 228. These computer/machine executable components (and other described herein) can be stored in memory associated with the one or more machines. The memory can further be operatively coupled to at least one processor, such that the components can be executed by the at least one processor to perform the operations described. Examples of said and memory and processor as well as other suitable computer or computing-based elements, can be found with reference to FIG. 10 (e.g., with reference to processing unit 1004 and system memory 1006), and can be used in connection with implementing one or more of the systems or components shown and described in connection with FIG. 1 or other figures disclosed herein.

System 200 can further include or be operatively coupled to an imaging system 202 and/or a picture archiving communication system (PACS) 204. The imaging system 202 can correspond to a 3D medical image system that captures and provides the scan data 102. For example, the imaging system 202 can correspond to a CT imaging system, an MR imaging system, or the like. Although a single imaging system is depicted, it should be appreciated that the imaging system 202 can correspond to a plurality of disparate imaging systems. In some embodiments, the reception component 220 can receive the scan data 102 directly from the imaging system 202. Additionally, or alternatively, scan data (e.g., scan data 102) provided by the imaging system 202 can be stored in one or more medical image databases 206 provided by the PACS 204 and the reception component 220 can extract the scan data 102 from the PACS 204.

System 200 can further include one or more user devices 230. The user device 230 can provide for accessing and employing the various output utilizations of related to the scan series characterization data 106. For example, the user device 230 can be or include a display capable of rendering medical image series included in the scan data 102 according to a visualization layout set up based on the scan series characteristics data 106. The user device 230 can also include suitable hardware and software that provides for communicating with various other components/system and modules of system 200 (e.g., via one or more wired or wireless communication networks), executing applications, and the like. In this regard, the type of the user device 230 can vary. For example, the user device 230 can be or include a server device, a personal computing device, a laptop computer, a desktop computer, a tablet computer, a smartphone, a television, a monitor, a wearable device, and the like. System 200 further includes a system bus 232 that can communicatively or operatively coupled the various systems, modules, components and devices of system 200. In some embodiments, the system bus 232 can include or correspond to one or more wired or wireless communication networks.

The architecture of system 200 can vary. For example, one or more components of the computing system 200 can be deployed on the same computing device (e.g., the scanner device/system used to acquire/capture and generate the input scan images). Additionally, or alternatively, one or more components of the computing system 200 can be deployed at different communicatively coupled computing devices (e.g., via one or more wired or wireless communication networks) in a distributed computing architecture.

The series characterization module 208 can perform the series characterization process described above with reference to FIG. 1. To facilitate this end, the series characterization module 208 can include image generation component 210, series characterization component 212, training component 214, characterization model database 216 and annotation component 218.

With reference to FIGS. 1 and 2, the image generation component 210 can generate the representative image 106 (or images) for each medical image series included in the scan data 102. In this regard, in some implementations, the scan data 102 may include only a single medical image series. With these implementations, the image generation component 210 can generate one or more representative images for the single series. For example, as applied to CT scan data, if the scan mode is cine, then the representative image can represent the one cycle of the acquisition. In other implementations, the scan data 102 may include two or more medical image series. With these implementations, the image generation component 210 can identify the different series included in the scan data 102 and generate a sperate representative image (or images) for each of the different series. For example, if the scan data 102 consists of multiple images at each image location obtained at different scan cycles/times as in a perfusion scan, then the image generation component 210 can generate one or more representative images for each group of images within that scan where within each group there is only image at each location. In another example, the scan data 102 may include multiple series of different anatomical regions in the body, which is often the case the trauma workflow (e.g., sometimes up to a dozen). In accordance with this example, the image generation component 210 can identify the different series and generate a separate representative image (or images) for each series.

For each series, the image generation component 210 may be configured to generate a single representative image from a single perspective/orientation of the 3D anatomy scan data. In other implementations, the image generation component 210 may be configured to generate two or more representative images that provide different views, have different slice thicknesses, have different visual properties, and so on. The number and type of representative images generated for a series can vary depending on the type of the series and other known information about the series. For example, in some implementations, some of the series characterization models can be adapted to process different representative input images that correspond to different views/perspectives of the 3D anatomy scan data. In other implementations, some of the series characterization models may be adapted to receive and process multiple input images (e.g., a multi-channel input model).

In some embodiments, the representative image or images can include one or more of the scan images included in the medical image series. With these embodiments, the image generation component 210 does not perform any image reconstruction/generation for obtaining the representative image(s). For example, the image generation component 210 can select the scan image included in the series that corresponds to the middle slice as the representative image. In another example, the image generation component 210 can select two or more scans at different scan locations for the representative images. For example, the image generation component 210 can select the middle slice plus the first slice and the last slice in the series as the representative images.

In other embodiments, the image generation component 210 can generate one or more new reconstructed images from the scan data 102 as the representative image or images using one or more 3D to 2D image compression techniques. The reconstructed image or images in these embodiments are referred to as "new" because they are not originally included in the scan data 102 and/or are not the type of 2D scan image reconstructions that the imaging system 202 is configured to generate. Instead, the image generation component 210 can generate the representative image (or images) from the 2D and 3D image data associated with the series as provided in the scan data 102.

In various embodiments, similar to the scan images in the series, the representative image generated by the image generation component 210 can include or correspond to an MPR image. In some implementations, the representative image can be considered an MPR image that uses the maximum intensity projection (MIP) for the pixel values in the final image, referred to herein as an MPR-MIP image. In other implementations, the representative image can be considered an MPR image that uses the minimum intensity projection (mIP) for the pixel values in the final image, referred to herein as an MPR-mIP image (using a lowercase m to denote minimum and an uppercase M to denote maximum). The type of the representative image (or images) can also vary for different anatomies and/or use-cases.

As noted above, the image generation process can be correlated to a 3D to 2D image compression process, wherein the image generation component 210 compresses a 3D volume image corresponding to a scanned anatomical region into a single 2D representation of that 3D volume image that captures the most important features of the 3D volume image. In various embodiments, this can involve selecting/defining a sub-volume of the 3D volume image for the compression and the orientation of the dimensionality of the compression (e.g., the specific axis or orientation for the 2D image relative to the 3D volume). For example, there are three standard anatomic planes that are generally used to display data for CT scans: axial (or horizontal), coronal (cutting the body into slices that go from anterior to posterior (AP) or posterior to anterior (PA)), and sagittal or lateral (cutting the body into slices that go from right to left or left to right). However, 2D CT scan images can also be generated relative to other planes (e.g., oblique or even curved planes). As described herein, reference to scan images being generated relative to one axis (e.g., x, y or z) of a 3D coordinate system refers to the scan images being generated at different points along the direction of the one axis such that each scan image is oriented relative to the same anatomical plane. The 3D volume image can be included in the scan data 102 and/or generated by the image generation component 210 by stacking the respective images included in the series.

In some embodiments, the image generation component 210 can be configured to generate the representative image in a default orientation (e.g., axial). For example, the default orientation can be based on the orientation of the medical image series. In this regard, if the medical image series includes axial scan images, then the image generation component 210 can select the axial orientation for the representative image. In other implementations, the image generation component 210 can be configured to generate representative images in two or more default orientations (e.g., axial, coronal AP, coronal PA, and/or sagittal/lateral). The orientation of the representative image or images can vary depending on the type of scan and the use-case. The process for compressing the 3D scan image data into the representative image can also vary based on the selected orientation for the representative image. Techniques for selecting the sub-volume of the 3D image data for which to perform the compression can also vary. In some embodiments, the image generation component 210 can be adapted to select a default sub-volume for any 3D volume image corresponding to the scanned region represented in a medical image series. For instance, the default sub-volume can remove a defined portion of the 3D volume in one or more directions in 3D from the boundary/periphery of the volume toward the centroid of the volume. In other implementations, the sub-volume selection can be based on the type of the scan, the specific anatomical region of interest scanned, the size/position of the subject, and other factors that may be known about the scan data 102.

Once the sub-volume and representative image orientation have been selected, the 3D-to-2D compression process can vary. In some implementations, the image generation component 210 can generate the representative image by selecting pixels from the 3D volume to be included in the MPR-MIP or MRP-mIP representative image based on the centroid of the sub-volume (or original volume). The image generation component 210 can also use a weighting function for the pixels, wherein pixels near the centroid of the selected sub-volume (or original volume) are given higher weights relative to peripheral pixels. The image generation component 210 may also select the range of pixels in the 2D directions of the selected orientation for the representative image (e.g., x and y, x and z, z and y, etc.) based on the particular anatomical region scanned and/or the type of the scan. For example, as applied to axial images, the image generation component 210 can select the range of pixels in the x and y direction based on the anatomy captured. The image pixels can also be optionally thresholded to include only a particular range of Hounsfield units (HU)s of interest (e.g., to avoid metal objects or bone if that is desired). The MPR-MIP/mIP representative images can also be generated with segmentation to remove non-patient related objects such as patient table or accessories. The image generation component 210 can also tailor the desired thickness for the representative scan image based on the orientation, anatomy and/or use-case.

Figure 3:
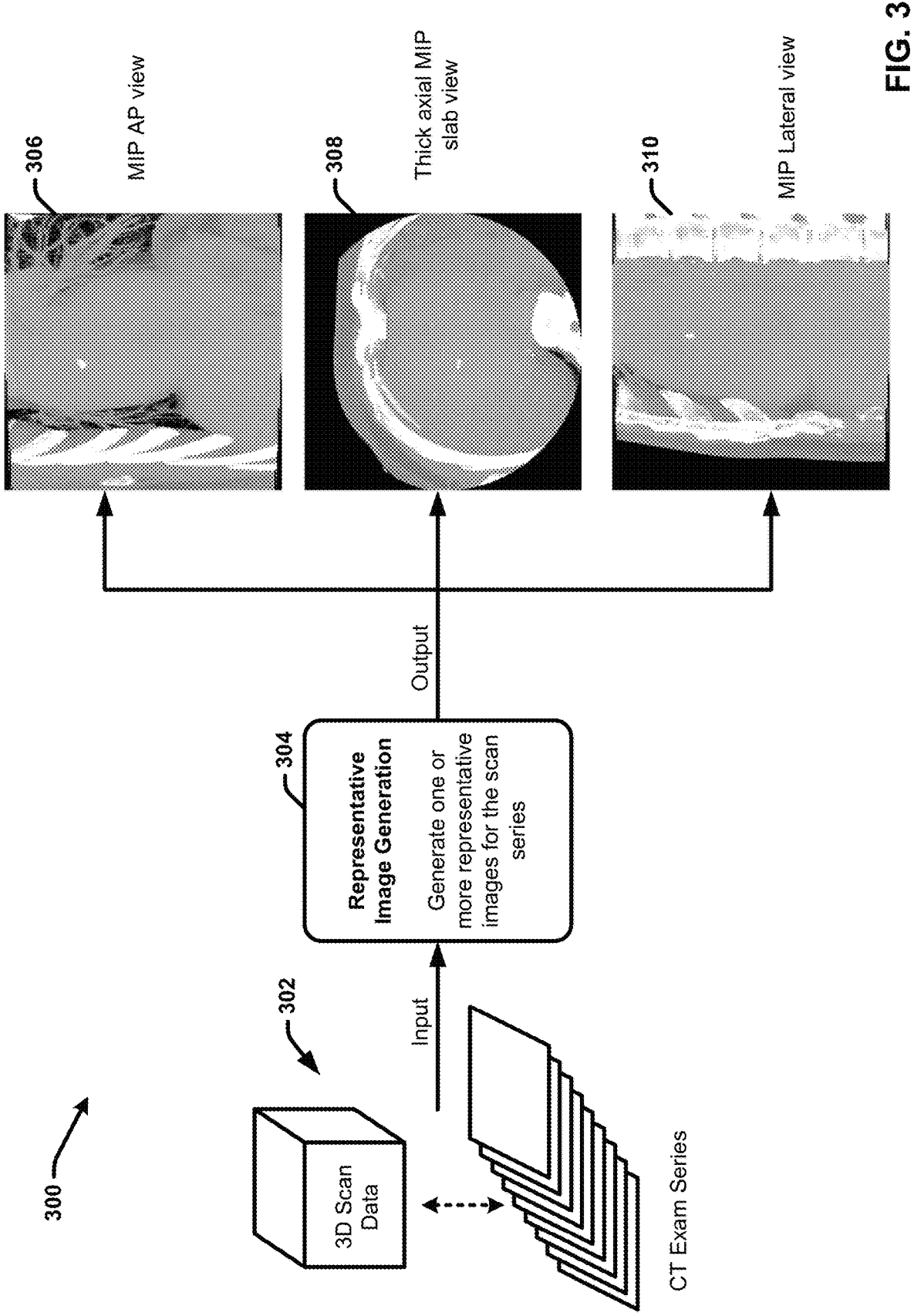
FIG. 3 illustrates an example process for generating one or more representative images for a medical image scan series in accordance with one or more embodiments of the disclosed subject matter.

FIG. 3 illustrates an example process 300 for generating one or more representative images for a medical image scan series in accordance with one or more embodiments of the disclosed subject matter. Process 300 illustrates three different types of example MRP-MIP representative images that can be generated (e.g., by the image generation component 210) for a cardiac CT exam study. In accordance with process 300, the input data 302 can include the CT exam series (which consists of a series of 2D MRP images) and/or the corresponding 3D scan data 302 that provides a 3D representation of the anatomical region scanned. Using this input data, at 304 the image generation component 210 can generate one or more representative images for the scan series using the techniques described above. In this example, the representative images include an MIP AP view 306, a thick axial MIP slab view 308 and an MIP lateral view 310.

The unique feature of these representations is the transformation of the series of images into single image weighted by the centroid values of pixels in the x and y directions so that the MPR-MIP image has the most representative view of the content of the human anatomy in the scanned series. This is very important for extremity scanning when the scanned anatomy may not be centered perfectly in the gantry. Also, various ranges of pixels in the x and y directions from the axial images may be optimally selected for different anatomies.

With reference again to FIG. 2, the series characterization component 212 can apply one or more series characterization models (or algorithms) to the representative image (or images) for each series to automatically detect and characterize defined characteristics of the series. These series characterization models can be included in the characterization model database 216 (or another suitable data structure accessible to the series characterization module 208. These series characterization models can include a plurality of different classification type models that have been trained to detect and characterize different characteristics or features included (or excluded) in the representative image (or images). The series characterization models can include various types of machine learning models that have been trained on training images corresponding to the representative image (or images) generated using the techniques described herein. The type or types of the machine learning models can vary. In some embodiments, the series characterization models can include deep learning models, such convolutional neural network (CNN)s, RESNET type models, and other neural network models with different types of pooling techniques in the classification block. Other suitable types of the machine learning models can include but are not limited to, generative adversarial neural network models (GANs), long short-term memory models (LSTMs), attention-based models, transformers, decision tree-based models, Bayesian network models, regression models and the like. These models may be trained using supervised, unsupervised and/or semi-supervised machine learning techniques.

In some embodiments, the series characterization module 208 may include training component 214 to train and develop the series characterization models based on training data provided by the medical image database 206 that includes accurately annotated scan data (e.g., with the characteristics that the models are being trained to detect). For example, the training data can include a plurality of different types of 3D imaging studies of the same modality (e.g., CT, MRI, PET, etc.) respectively including different types of medical image series, captured with different protocols and performed for a plurality of different patients. For each of the medical image studies in the training data, the image generation component 210 can employ the same representative image generation techniques to generate the representative images for training the respective series characterization models. The model training process can generally be performed offline as a sperate phase prior to the inferencing phase in which the series characterization models are applied to the representative images in the field to generate the scan series characteristics data 106. In some embodiments, the training component 214 can also regularly and/or continuously retrain and fine tune the series characterization models over time (after deployment) based on received user feedback regarding the accuracy of the model performance on new scan series data.

In one or more embodiments, the series characterization models can include a plurality of different models tailored to different scan types, anatomical regions, and classification tasks. The series characterization component 212 can select and apply the appropriate models for a particular set of scan data 102 and/or medical image series associated therewith based on any known information about the series (as received as metadata with the scan data 102) and inferred information learned about the medical image series as a result of application of a one or more of the series characterization models. In this regard, the series characterization component 212 can apply at least some of the series characterization models in a sequential fashion, wherein the inference output of a preceding model influences the selection of the following model. For example, based on a first model indicating a series depicts a specific anatomical ROI, the series characterization component 212 may select and apply a second series characterization model to the representative image (or images) based on the second model being tailored to that specific anatomical ROI, wherein the second model is adapted to detect another characteristics about the series. The series characterization component 212 can continue to select and apply additional models to the representative image (or images) in this fashion as applicable based on the outputs of the preceding models. The number of series characterization models applied, and the characteristics inferred by each model can vary.

In various embodiments, the series characterization models can include one or more primary models adapted to detect or classify the series type. With these embodiments, the series type can be one of a predefined set of series type classifications. The number and description of the series type classifications can vary depending on the scan modality (e.g., CT, MR, PET, etc.), and the system design. In one or more embodiments as applied to CT scans, the series type can be one of about 8-20 predefined type classifications that are based on the anatomical region or body part captured in the series.

Figure 4A:
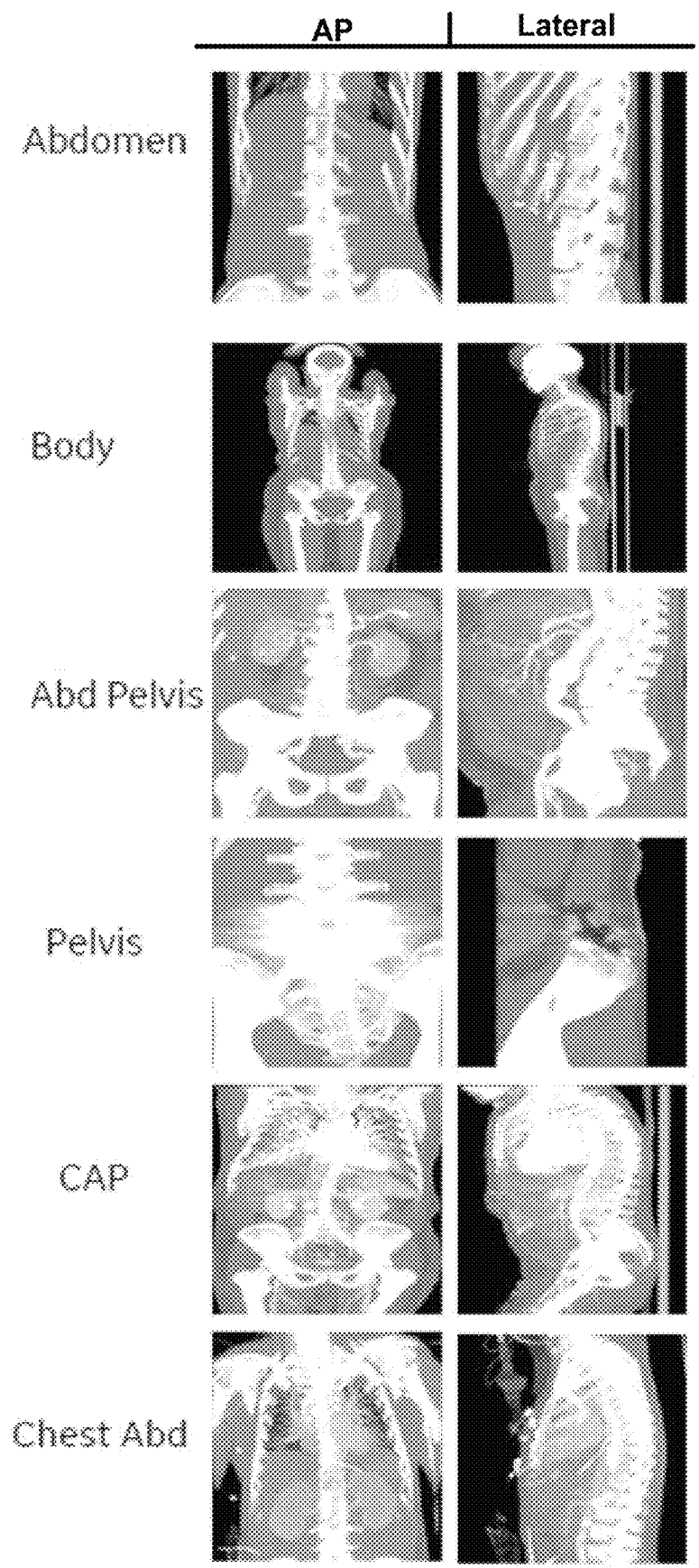
FIGS. 4A-4C present example scan representative images generated for different medical image series type classifications in accordance with one or more embodiments of the disclosed subject matter.
Figure 4B:
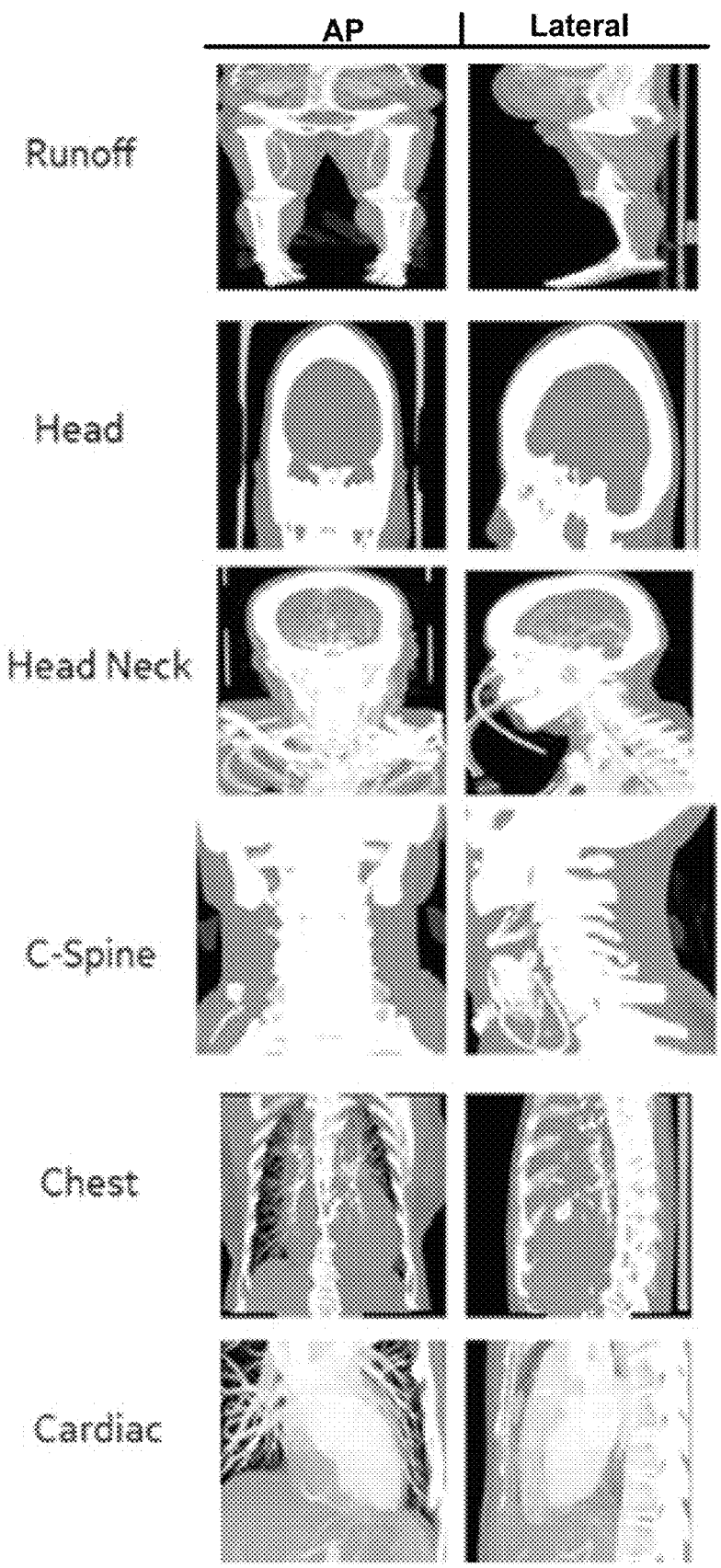
Figure 4C:
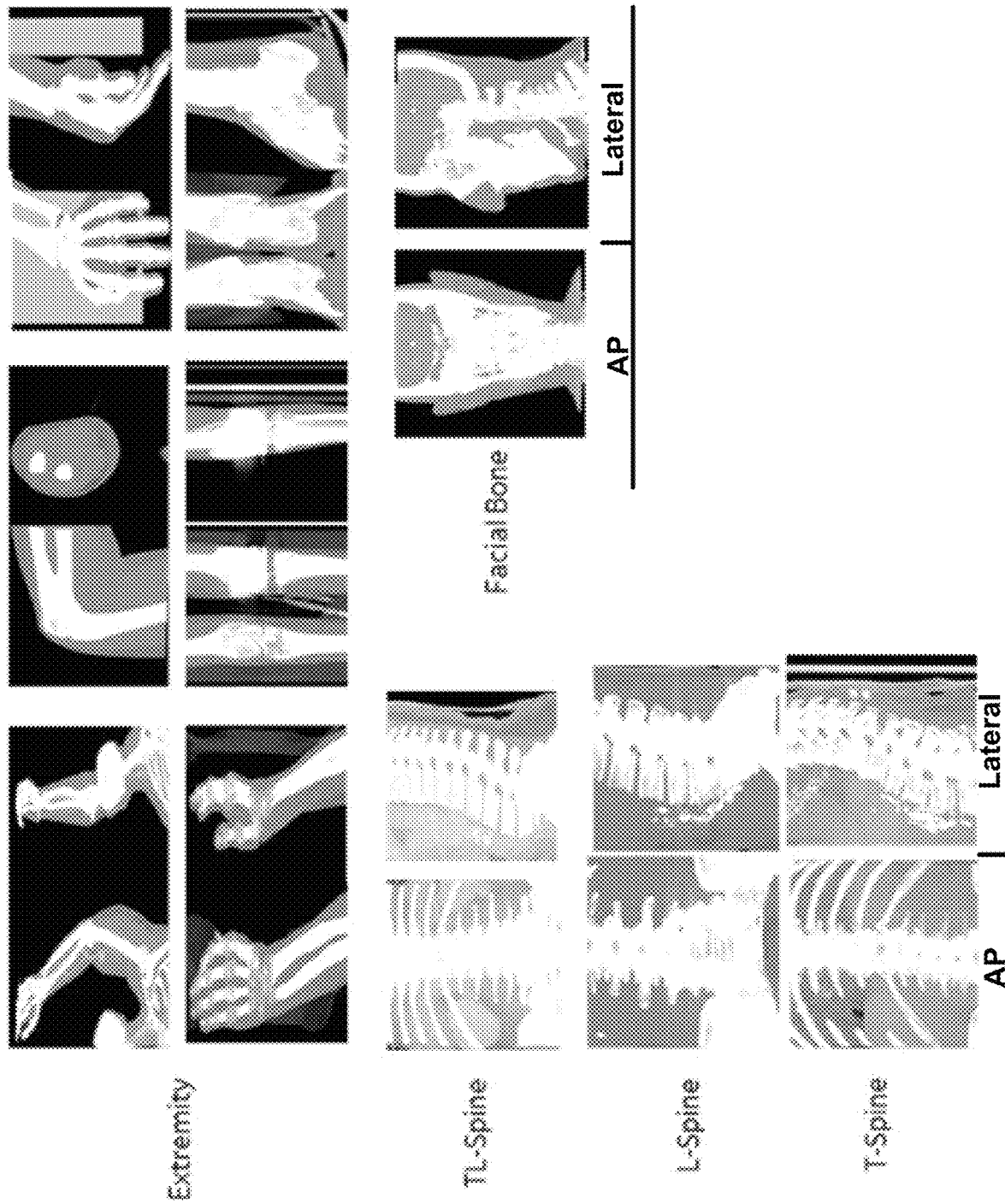

FIGS. 4A-4C illustrate example MPR-MIP representative images generated using the techniques described above for different series type classifications. The series type classifications in this example include: abdomen, body, abdomen/pelvis, pelvis, CAP (chest, abdomen and pelvis), chest/abdomen, runoff, head, head/neck, C-spine, chest, extremity, TL-spine, L-spine, T-Spine, and facial bone. In this example, aside from the extremity category, the image generation component 210 has generated two representative input images for each series category, one from the AP perspective and another from the lateral perspective. These example representative images can be used as input to the various series characterization models to detect the series type classification along with various other characteristics discussed below.

With reference again to FIG. 2 in view of FIG. 4, in one or more embodiments, the series characterization component 212 can be configured to initially apply one or more series type classification models to the representative image (or images) generated for a series to determine the series type classification. The series characterization model 212 can then select and apply one or more secondary series characterization models to the representative image (or images) based on the series type classification. With these embodiments, the secondary series characterization models can include different subsets of models that are tailored to different series types. In some implementations of these embodiments, the series characterization models can include a universal type classification model that can receive any representative image (e.g., any of the representative images depicted in FIGS. 4A-4C for instance), regardless of the anatomical region depicted, and generate an output classification that classifies the series type as one of the possible type classification categories.

In other embodiments, the series characterization models can include separate models for each of the different type classifications and the series characterization component 212 can be configured to apply each of the models to the representative image (or images) to determine which one provides a positive classification. In some implementations of these embodiments, in order to minimize errors attributed to false positives and/or false negatives, the different series type classification models can be adapted to generate a binary output that classifies the input images as either having or not having the specific type classification that the model is adapted to detect and a confidence score indicative of the degree of confidence in the accuracy of the model's output. For example, assume there are 15 different series type classification models each adapted to classify the representative image (or images) as either having (e.g., a positive classification) or not having (e.g., a negative classification) the specific series type classification the model is adapted to detect and provide a confidence score reflective of the degree of confidence in the result (e.g., as a percentage score with 0% being the lowest degree of confidence and 100% being the highest, or another suitable scoring scale). The series characterization component 212 can further evaluate the results of each of the models to select the most probable classification based on the binary classification and the confidence score. For example, in some implementations, if only one model provides a positive result, the series characterization component 212 can assume the series belongs to that series classification. However, if there is more than one positive result, the series classification component 212 can select the classification with the highest confidence score.

Additionally, or alternatively, the series classification component 212 can select the top N positive results (e.g., top two or another number) with the top N highest confidence scores as possible type classifications for the series for further processing with additional more refined type classification models tailored to those categories to further drill down on the correct series type classification. In some implementations of these embodiments, the image generation component 210 can generate one or more additional or alternative representative images for the series based on the potential type classification categories, wherein the additional representative images are tailored to the potential type classification categories. For example, the image generation component 210 can tailor the representative image generation parameters (e.g., the sub-volume dimensions, the directionality/orientation, the pixel weightings, the type of the projection (MIP vs. mIP) and so on) based on the potential type classifications to generate one or more new representative images that are tailored to the potential type classifications. For instance, if the potential type classifications include chest and cardiac, the image generation component 210 can generate one or more new representative images for the series that better represent the distinguishing characteristics between chest and cardiac. The series characterization component 212 can then reapply the corresponding series type classification models to the new representative images to drill down on the correct classification. The image generation component 210 can also generate one or more new representative images with different image generation parameters for processing by the primary and/or secondary series characterization models based on measure of confidence in the model outputs. For example, in some implementations, the series characterization models can be adapted to generate a confidence score that reflects the level of confidence in the accuracy of the model output. The image generation component 210 can further be adapted to generate one or more new representative images with different orientations/perspectives (or other image generation parameters) for processing by the models based on the confidence score being below a threshold level of confidence. For example, in the case of ambiguity of a prediction from a first series characterization model with one type of representative image in a first orientation (e.g., anterior posterior (AP)), the image generation component 210 can generate another representative image in a different orientation (e.g., lateral) for processing by the first series characterization model (or a different series characterization model) to provide an additional inference output get down to a more definitive classification. The different outputs can further be aggregated to converge on a more accurate classification.

In some embodiments, the secondary series characterization models can include one or more contrast phase detection models adapted to detect whether contrast injection was performed and if so, the particular contrast phase reflected in the series. The contrast phases can be classified as one of a defined set of possible contrast phases. For example, in some implementations, the defined set can include either non-contrast, arterial, portal/venous, and delayed. In other implementations, the defined set can include two or more of the following phases: pre-contrast phase (or unenhanced phase), intravenous (IV) phase (IVP), arterial phase (AP), early AP, late AP, extracellular phase (ECP), portal venous phase (PVP), delayed phase (DP), transitional phase (TP), hepatobiliary phase (HBP), and variants thereof. As noted above, these contrast phase detection models can include different models tailored to different series type classification. In this regard, the series characterization component 212 can select the appropriate contrast phase detection model (or models) for applying to the representative image (or images) based the series type classification. For example, the contrast phase detection models can be optimized by anatomy. Accordingly, if a first series characterization model detects a particular anatomical ROI and/or landmark present, the series characterization component 212 can invoke the contrast phase detection model for that anatomical ROI and/or landmark (e.g., cardiac, head, abdomen, etc.). The number of clinically relevant contrast phases present in a series often vary by anatomical region. Thus, by tailoring the different contrast phase detection models to specific anatomies, the respective models will be adapted to detect the appropriate clinically relevant contrast phases.

The secondary series characterization models can also include one or more artifact detection models adapted to detect whether any artifacts are depicted in the representative image (or images) and thus the series. These artifacts can include metal implants/devices as well as other foreign objects present in the body. In some implementations, the one or more artifact detection models can also be adapted to classify the type of artifact/object detected and/or the relative anatomical location of the detected artifact. As noted above, in some embodiments, the one or more artifact detection models can include different models tailored to different series type classifications and/or contrast phases. In this regard, the series characterization component 212 can select the appropriate artifact detection model (or models) for applying to the representative image (or images) based the series type classification and/or the contrast phase classification.

The secondary series characterization models can also include one or more anatomy classification models adapted to classify specific anatomical features and/or ROIs depicted in the representative image (or images) and thus the series. The anatomy classification models can provide a more granular anatomy classification relative to the series classification models. Similar to the other secondary classification models, in some embodiments, the one or more anatomy detection models can include different models tailored to different series type classifications and/or contrast phases. In this regard, the series characterization component 212 can select the appropriate anatomy classification model (or models) for applying to the representative image (or images) based the series type classification and/or the contrast phase classification.

The secondary series classification models can also include additional characterization models adapted to detect additional anatomy specific and/or contrast phase specific characteristics of a medical image series based on the representative image (or images). For example, some additional characteristics can include, but are not limited to, image quality characteristics such as banding artifacts, rings, streaks, etc., and relative position and alignment of specific anatomical landmarks that are relevant to a particular type of scan (e.g., alignment position of head for a brain scan).

In some embodiments, the image generation component 210 can also generate one or more additional or alternative representative images for the series based on its type classification, contrast phase classification, and/or other inferred characteristics for input to an additional secondary series characterization model, wherein the additional representative images or images are tailored to the other additional series characterization model. For instance, the image generation component 210 may generate a new representative image for a series based on its series type classification for input to a contrast phase detection model and/or artifact detection model. With these embodiments, the image generation component 210 can tailor the new representative image generation parameters (e.g., the sub-volume dimensions, the directionality/orientation, the pixel weightings, the type of the projection (MIP vs. mIP), and so on) based on its type classification to generate one or more new representative images that are tailored to the type classifications.

The result of the series characterization process can include one or more automatically detected characteristics of the respective series included in the scan data 102. The annotation component 218 can further generate annotation metadata (e.g., scan series characteristics data 106) describing the one or more characteristics and associate the annotation metadata with the respective series as stored in one or more databases (e.g., the medical image database 206 or another suitable database). The annotation component 218 can further structure the annotation metadata according to a defined protocol or format, such as the DICOM standard or a similar standard.

The scan series characteristics data 106 can further be employed to automatically invoke applicable post-processing tasks, image analysis task, and reporting tasks as well as optimize the visualization workflows.

In this regard, the system 200 can include visualization component 222 to facilitate reviewing the medical image series via a medical imaging application accessed via the user device. For example, the medical imaging application can include a web-application, a native application, a hybrid application or the like, that provides for accessing medical image series provided in the medical image database 206, reviewing/viewing the medial image series, generating radiologist reports, annotating the medical images, and/or executing various post-processing tasks on the images. In some implementations, the visualization component 222 can include or otherwise provide the medical imaging application. In this regard, many existing medical imaging applications require the user (e.g., the radiologist, the technician, etc.) to manually select and set up the visualization layout as desired based on the series type, the contrast phase present and other characteristics about the series. With the disclosed techniques, the visualization component 222 can automatically generate the visualization layout as tailored to the medical image series based on the automatically detected scan characteristics. For example, the visualization component 222 can determine the number of windows, the size of the respective windows, the different images or groups of images to include in the respective windows, the different image views/perspectives to include in the respective windows, the annotation tools to provide/activate, the editing tools to provide/activate, and so on, based on the series type classification, the contrast phase or phases detected, and other automatically detected scan characteristics. The visualization component 222 can also include (or the user device can include) a rendering component that renders the medical image series according to the visualization layout in association with reviewing the medical image series via the medical imaging application.

Figure 5:
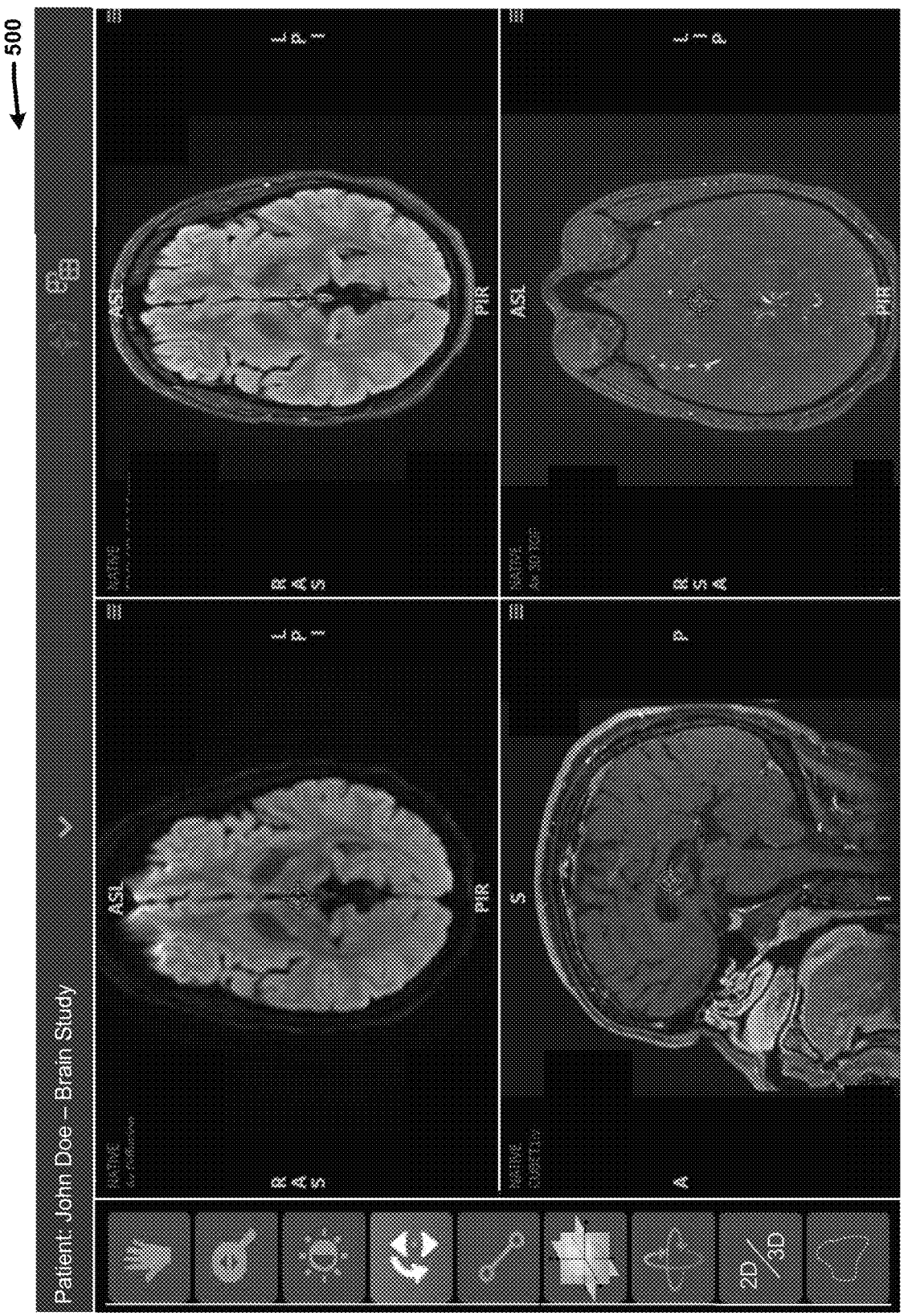
FIG. 5 present an example visualization layout for a brain scan series in accordance with one or more embodiments of the disclosed subject matter.
Figure 6:
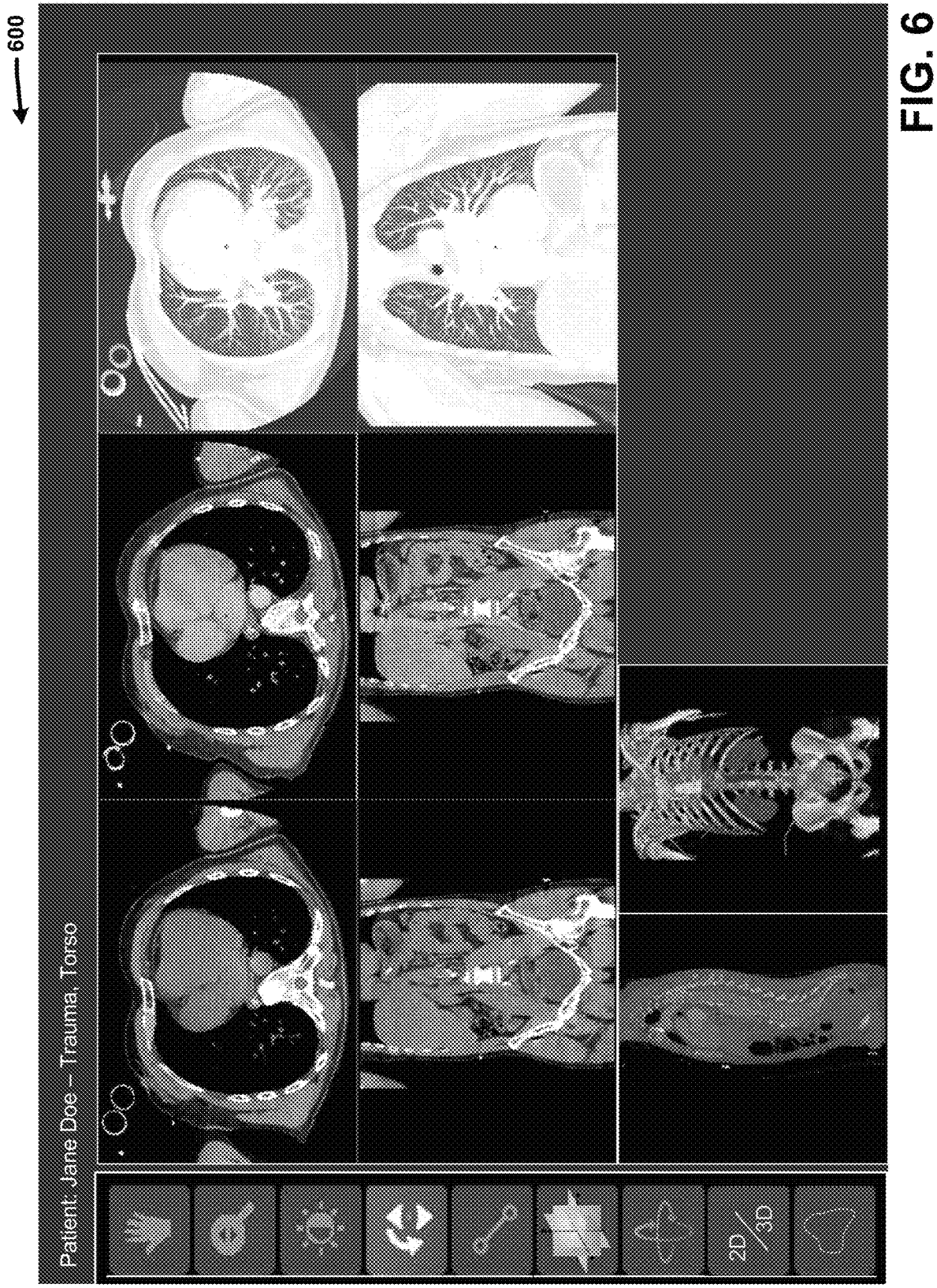
FIG. 6 present an example visualization layout for a trauma torso series in accordance with one or more embodiments of the disclosed subject matter.

For example, FIG. 5 present an example visualization layout 500 for a brain scan series that may be generated by the visualization component 222 based on automatically detected scan characteristics of the brain scan series. FIG. 6 present another example visualization layout 600 for a trauma torso series that may be generated by the visualization component 222 based on automatically detected scan characteristics of the trauma torso series. As can be seen by comparison of visualization layout 500 and 600, the design of the layout can vary significantly for different types of series.

With reference again to FIG. 2, in addition to automatically tailoring the visualization layout and tools, the system 200 can also include a feedback component 224 that can provide the scan series characteristics data 106 as feedback data to an operating technician of the medical imaging system 202 (e.g., the canner device) to facilitate reviewing whether the medical image series reflects one or more target characteristics for the performance of the scan while the patient is positioned relative to the medical image scanner device. For example, the reception component 220 can receive the scan data 102 for processing by the series characterization module 208 while the patient is still laying on the scanner table. The inferred scan series characteristics data 106 can further be provided to the operating technician via a computing device employed by the technician (e.g., user device 230) prior to completion of the scanning session. The technician can then review the results and determine whether to rescan the patient as needed to obtain the desired scan characteristics. Additionally, or alternatively, the scan series characteristics data 106 can be presented to the technician in association with an automated annotation software tool that facilitates more efficiently entering annotation tags for a scan series by the technician in accordance with a standardized protocol (e.g., DICOM or the like). For example, as opposed to manually entering individual scan characteristic DICOM tags for a medical image series, the software can allow the technician to review the automatically detected characteristics and either accept and apply the annotation to the medical image series, edit the detected characteristics or reject the characteristics.

The similar case study component 226 can further provide for automatically finding and pulling similar cases for a current medical image series based on the automatically detected scan characteristics. In particular, the similar case study component 226 can accesses a medical image database comprising a plurality of different medical image studies (e.g., medical image database 206), identify a subset (e.g., one or more) of the different medical images studies that are similar to the medical image series based on the one or more characteristics, and extract the subset for performance of comparative analysis between the subset and the medical image series. For example, the similar cases can be presented to a radiologist (or another reviewing entity) via the visualization application in association with reviewing the current medical image series. In another example, the similar cases can be aggregated and used for additional post-processing tasks and applications (e.g., model training, receiving expert review, used for continued learning and reporting, etc.). In some implementation, the similar case study component 226 can also be configured to find and pull similar medical image exams (e.g., series) for the same patient for the purpose of performing longitudinal studies. In this regard, the similar case study component 226 can employ an identifier for the patient associated with the current medical image series and find and pull (e.g., extract) other cases for the same patient identifier that were performed in the past and have one or more of the same or similar series characteristics (e.g., same series type, same contrast phase, etc.).

The post-processing component 228 can also select and apply one or more post-processing tasks for processing the medical image series based on the one or more automatically detected scan series characteristics. The types of the post-processing tasks can vary. For example, the post-processing tasks can include automatic application of one or more image processing models/algorithms adapted to process medical images in the series. These image processing algorithms can include various medical image inferencing algorithms or models (e.g., AI models). For example, the image processing algorithms can include, but are not limited to, image restoration algorithms (e.g., used to improve the quality of the image), image analysis algorithms (e.g., classification/diagnosis models, organ segmentation models, etc.), image synthesis algorithms (e.g., used construct a three-dimensional image based on multiple two-dimensional images images), image enhancement algorithms (e.g., used improve the image by using filters or adding information that will assist with visualization), and image compression algorithms (e.g., used to reduce the size of the image to enhance transmission times and storage required). The post-processing component 228 can automatically invoke and apply the appropriate image processing models for a series based on the specific scan characteristics automatically detected by the series characterization models. For example, in an implementation in which a series characterization model includes an artifact detection model that detected presence of an artifact in the one or more representative images, the post-processing component 228 can automatically select and apply an artifact reduction/correction image processing model on one or more of the original images in the series to remove/correct artifacts included therein. Further, the artifact reduction/correction image processing models can be tailored to specific types of anatomies and/or specific types of artifacts. In this regard, the post-processing component 228 can select and apply the appropriate artifact reduction/correction image processing model based on the detected series type, anatomy present, and the specific type of artifact detected.

The image processing algorithms may be stored at one or more network accessible locations (not shown) that may be accessed and applied by the post-processing component 228. In various embodiments, the image processing algorithms can be integrated into the predefined workflows as HTTP tasks and accessed and applied to the medical images as web-services in accordance with the pre-defined workflows. The pre-defined workflows can be tailored to specific medical image series types and other characteristics of the medical image series that are capable of being automatically detected by the series characterization module 208. Additionally, or alternatively, the algorithms/models can be integrated into workflows as "jobs." Specifically, an algorithm/model and other tasks defined by computer executable instructions can be wrapped in a Kubernetes Job function and the algorithm orchestration component can execute it asynchronously inside the cluster on behalf of the user. This feature opens multiple possibilities specially related to legacy systems where the client service is not under HTTP and is only a simple command line and/or executable.

Figure 7:
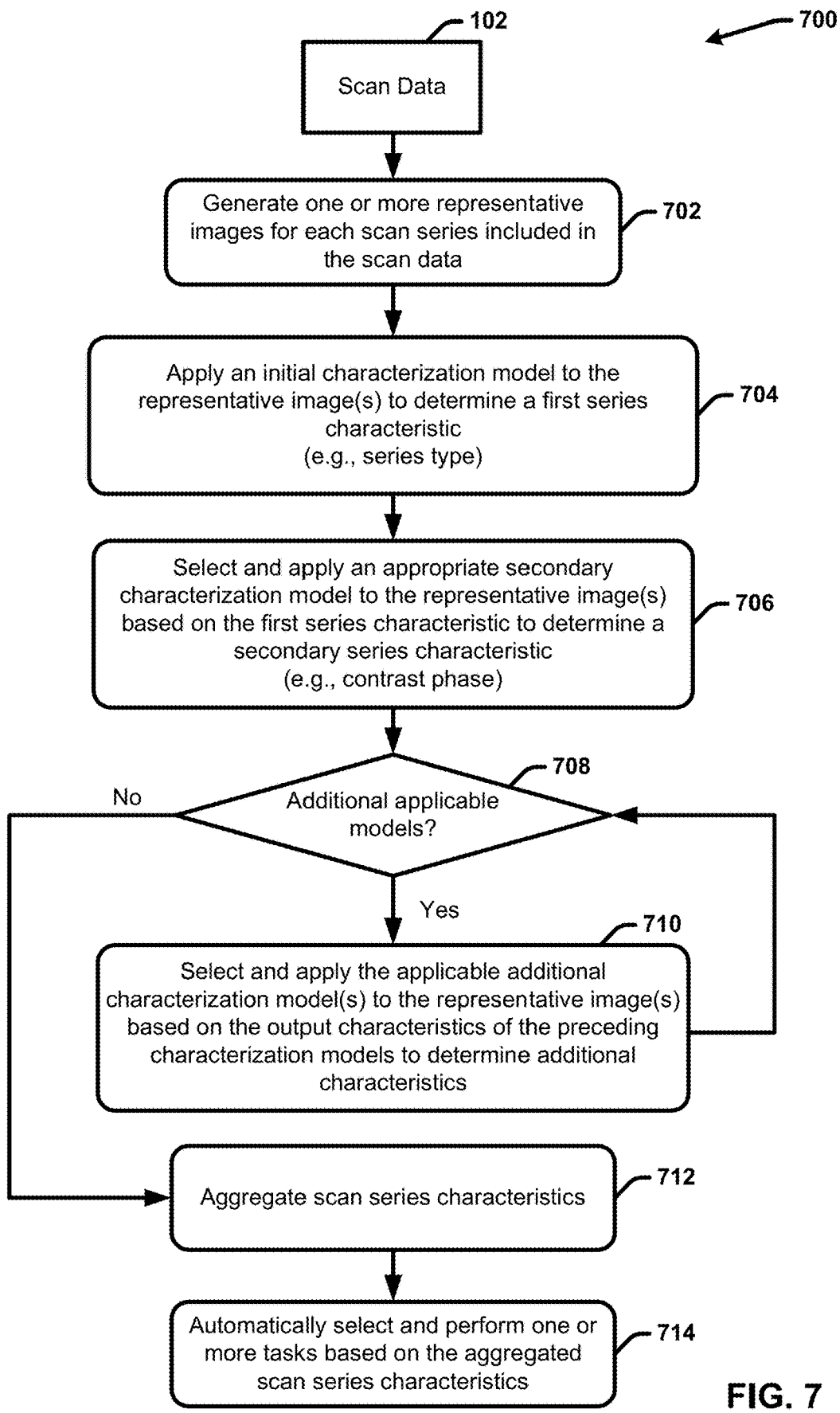
FIG. 7 illustrates a flow diagram of an example process for automatically detecting scan characteristics of a medical image series in accordance with one or more embodiments of the disclosed subject matter.

FIG. 7 illustrates a flow diagram of an example process 700 for automatically detecting scan characteristics of a medical image series in accordance with one or more embodiments of the disclosed subject matter. Process 700 provides an example process that can be performed by system 200. In accordance with process 700 at 702, the system can generate one or more representative images for each scan series included in the scan data 102. For each scan series, at 704, the system can apply an initial characterization model to the representative image to determine a first series characteristic (e.g., series type). At 706, the system can select and apply an appropriate secondary characterization model to the representative image based on the first series characteristic to determine a secondary series characteristic (e.g., contrast phase). At 706, the system can determine whether any additional series characteristic models are available that are applicable to the scan series based on the output of the preceding models. If not, then process 700 can aggregate the scan series characteristics at 712. If additional models are applicable, then at 710, the system can select and apply the applicable additional characterization model(s) to the representative image(s) based on the output characteristics of the preceding characterization models to determine additional characteristics. The system can repeat this process until all applicable models have been applied in a daisy-chain fashion. Once all applicable models have been applied and the characteristics have been aggregated, at 714, the system can automatically select and perform one or more tasks based on the aggregated scan series characteristics.

Figure 8:
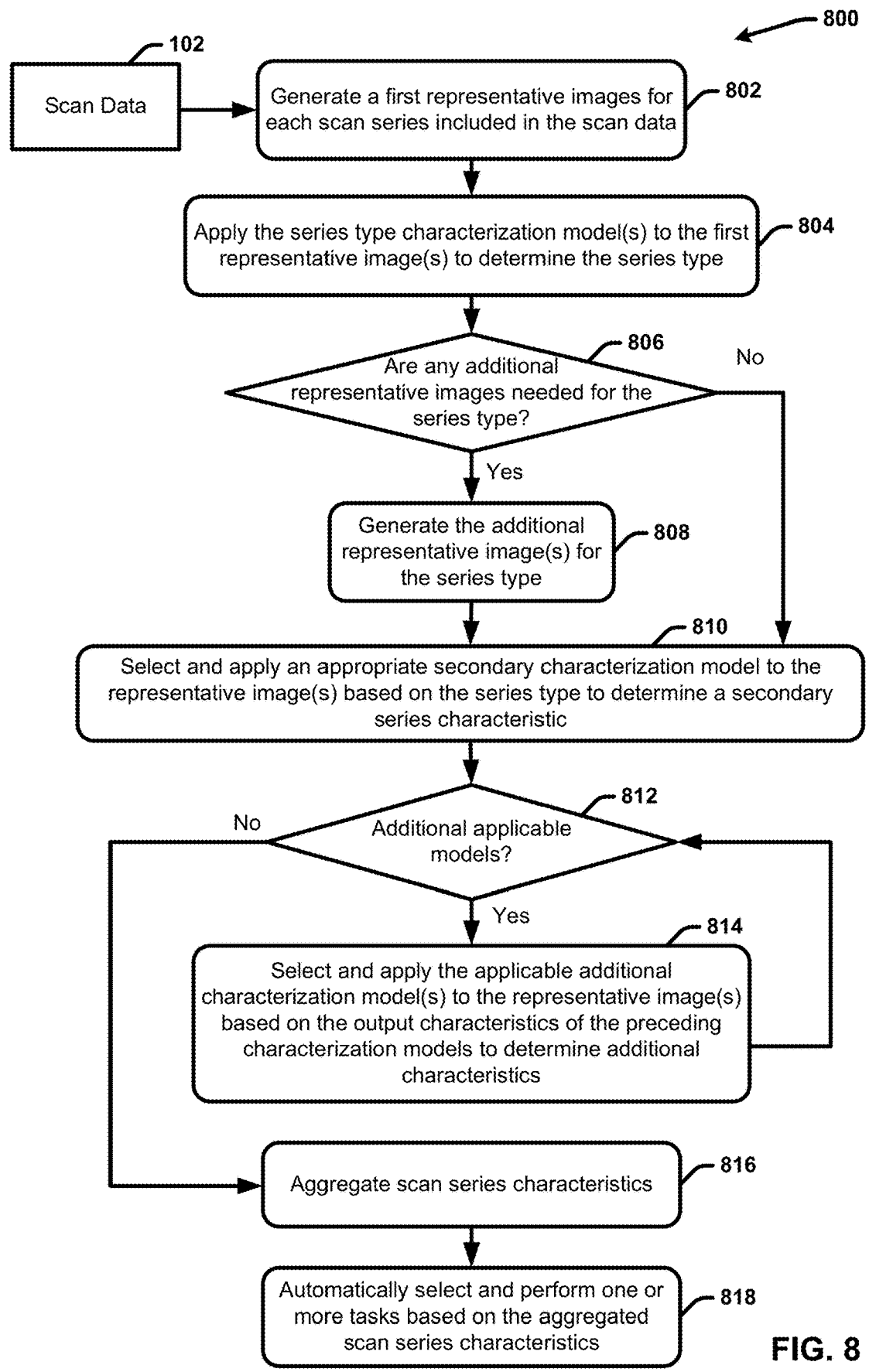
FIG. 8 illustrates a flow diagram of another example process for automatically detecting scan characteristics of a medical image series in accordance with one or more embodiments of the disclosed subject matter.

FIG. 8 illustrates a flow diagram of another example process 800 for automatically detecting scan characteristics of a medical image series in accordance with one or more embodiments of the disclosed subject matter. Process 800 provides another example process that can be performed by system 200. In accordance with process 800 at 802, the system can generate a first representative image for each scan series included in the scan data 102. For example, the first representative image may include a default MPR-MIP reconstruction using reconstruction parameters that are not anatomy specific. For each scan series, at 804, the system can apply the one or more series type characterization models to the first representative image to determine the series type. At 808, the system can determine whether any additional representative images are needed for the series type. For example, the series characterization component 212 can determine based on the series type, what types and characteristics of representative images are needed as input to subsequent available series characterization models for that series type and direct the image generation component 210 to generate new or additional representative images with reconstruction parameters that are tailored to that series type (e.g., anatomy specific). In this regard, at 806, if no additional representative images are needed, then process 800 can continue to 810. However, if additional representative images are needed for the particular series type, then at 808, the system can generate the additional representative image (or images) for the series type.

At 810, the system can select and apply an appropriate secondary characterization model to the representative image based on the series type to determine a secondary series characteristic (e.g., contrast phase). At 812, the system can determine whether any additional series characteristic models are available that are applicable to the scan series based on the output of the preceding models. If not, then process 800 can aggregate the scan series characteristics at 816. If additional models are applicable, then at 814, the system can select and apply the applicable additional characterization model(s) to the representative image(s) based on the output characteristics of the preceding characterization models to determine additional characteristics. The system can repeat this process until all applicable models have been applied in a daisy-chain fashion. Once all applicable models have been applied and the characteristics have been aggregated, at 818, the system can automatically select and perform one or more tasks based on the aggregated scan series characteristics.

Figure 9:
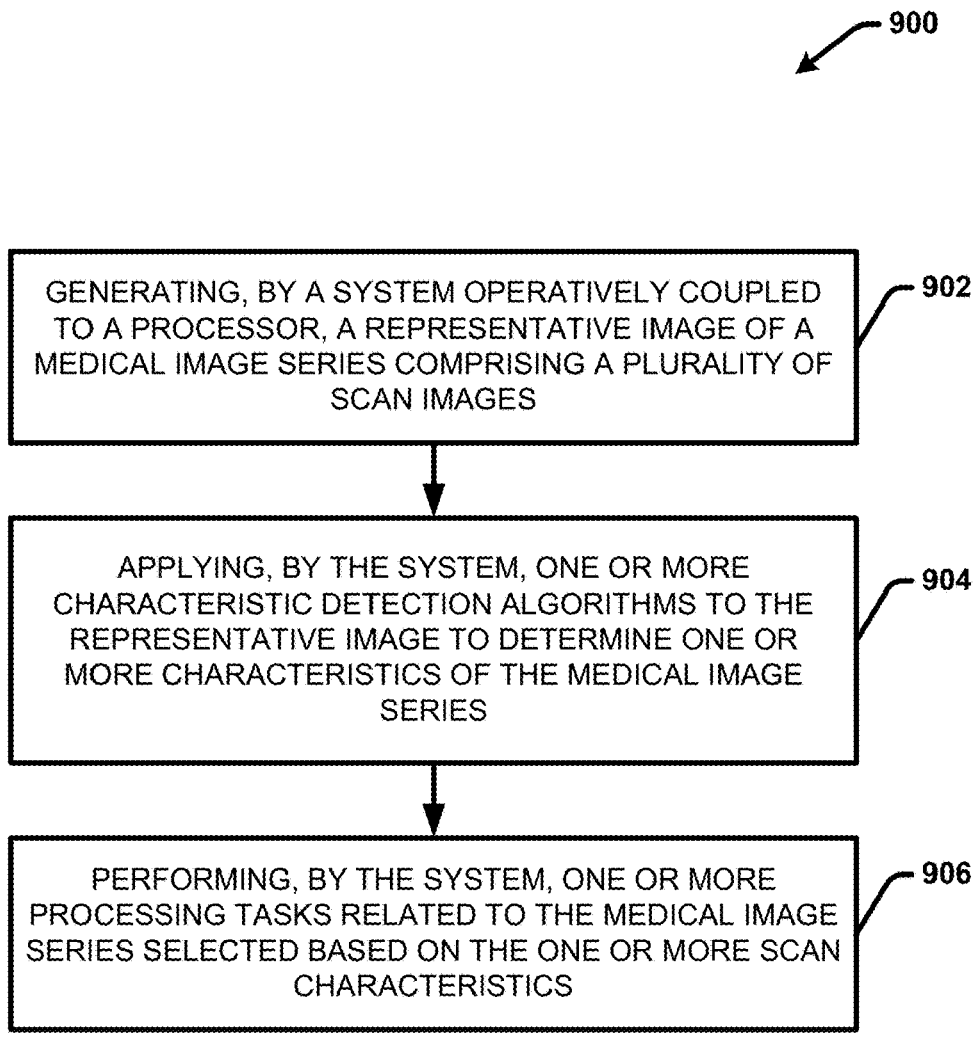
FIG. 9 illustrates a high-level flow diagram of another example process for automatically detecting scan characteristics of a medical image series in accordance with one or more embodiments of the disclosed subject matter.

FIG. 9 presents a high-level flow diagram of an example computer-implemented process 900 for automatically detecting scan characteristics of a medical image series in accordance with one or more embodiments of the disclosed subject matter. Repetitive description of like elements employed in respective embodiments is omitted for sake of brevity.

In accordance with process 900, at 902 a system operatively coupled to a processor (e.g., system 100 or the like), generates a representative image of a medical image series comprising a plurality of scan images (e.g., using image generation component 210). At 904, the system applies one or more characteristic detection algorithms to the representative image to determine one or more characteristics of the medical image series (e.g., using series characterization component 212). At 906, the system performs one or more processing tasks related to the medical image series selected based on the one or more scan characteristics (e.g., using visualization component 222, feedback component 224, similar case study component 226, and/or post-processing component 228).

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
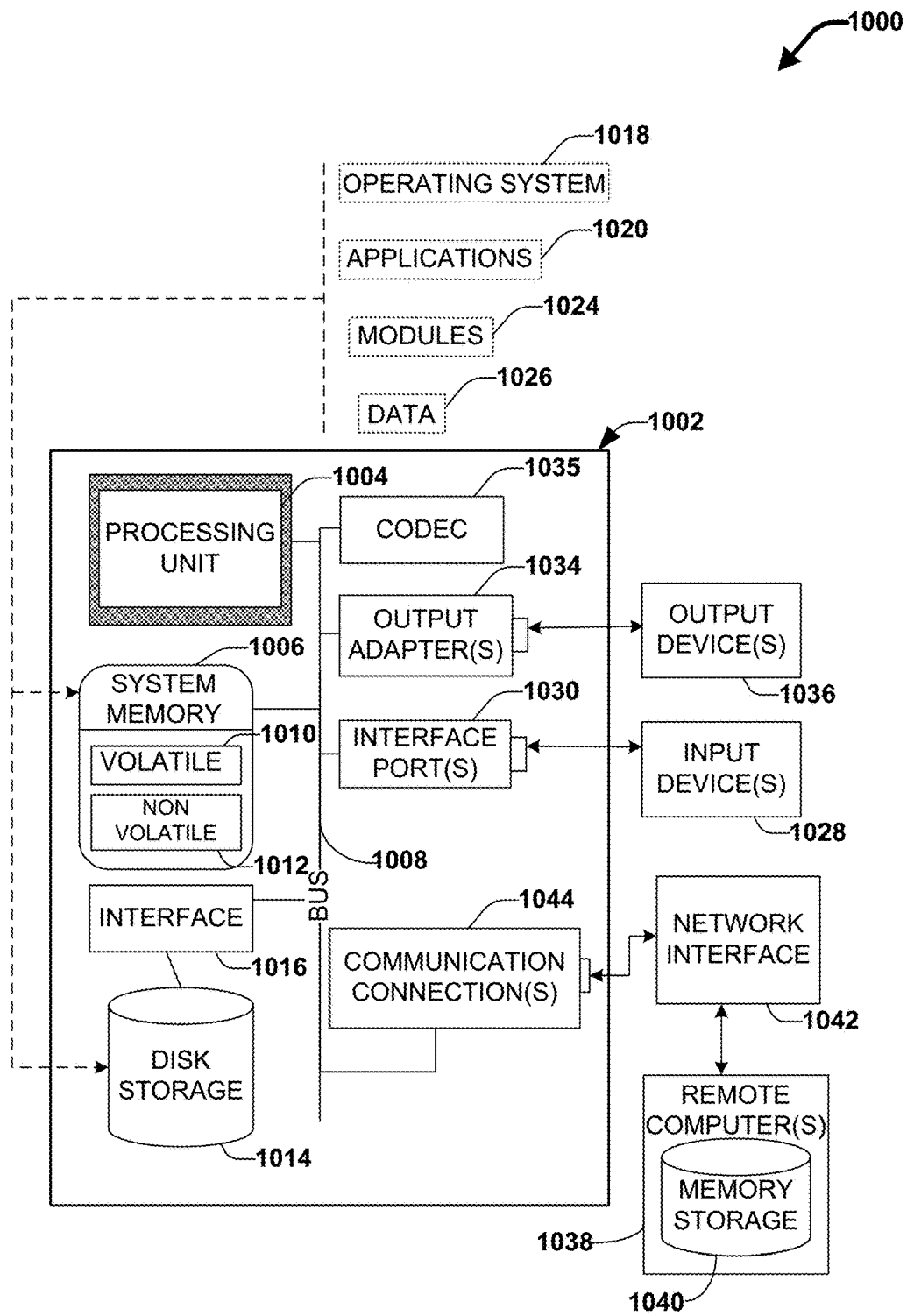
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1094), and Small Computer Systems Interface (SCSI).

The system memory 1006 includes volatile memory 1010 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1010 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1014 to the system bus 1008, a removable or non-removable interface is typically used, such as interface 1016. It is appreciated that disk storage 1014 can store information related to a user. Such information might be stored at or provided to a server or to an application running on a user device. In one embodiment, the user can be notified (e.g., by way of output device(s) 1036) of the types of information that are stored to disk storage 1014 or transmitted to the server or application. The user can be provided the opportunity to opt-in or opt-out of having such information collected or shared with the server or application (e.g., by way of input from input device(s) 1028).

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
   an image generation component that generates one or more representative images of a medical image series comprising a plurality of scan images, wherein the medical image series is associated with three-dimensional (3D) image data representative of a 3D volume of an anatomical region of a patient, wherein each of the plurality of scan images correspond to different slices of the 3D volume, and wherein the image generation component generates the one or more representative images from the 3D image data using a 3D to two-dimensional (2D) image compression processes that comprises generating a representative image of the one or more representative images using pixels included in the 3D image data and a weighting function for the pixels based on relative distances of the pixels to a centroid of the 3D image volume; and
   a series characterization component that processes the one or more representative images using one or more characteristic detection algorithms to determine one or more characteristics of the medical image series, wherein the one or more characteristics comprise a type of the medical image series classified from amongst different defined types of medical image series.

2. The system of claim 1, wherein the computer executable components further comprise:
   an annotation component that generates annotation metadata describing the one or more characteristics and associates the annotation metadata with the image series as stored in one or more databases.

3. The system of claim 1, wherein the computer executable components further comprise:
   a visualization component that generates a visualization layout for reviewing the medical image series via a medical imaging application based on the one or more characteristics, wherein the visualization layout varies for the different defined types; and
   a rendering component that renders the medical image series according to the visualization layout in association with reviewing the medical image series via the medical imaging application.

4. The system of claim 1, wherein the computer executable components further comprise:
   a post-processing component that selects and applies one or more post-processing tasks for processing the medical image series based on the one or more characteristics, wherein the one or more post-processing tasks comprise one or more clinical inferencing tasks performed using one or more clinical inferencing models.

5. The system of claim 1, wherein the computer executable components further comprise:
   a similar case study component that accesses a medical image database comprising a plurality of different medical image studies, identifies a subset of the different medical images studies that are similar to the medical image series based on the one or more characteristics, and extracts the subset for performance of comparative analysis between the subset and the medical image series.

6. The system of claim 1, wherein the computer executable components further comprise:
   a reception component that receives the medical image series in association with performance of a 3D imaging scan of a patient while the patient is positioned relative to a medical image scanner device; and
   a feedback component that provides feedback data describing the one or more characteristics to an operating technician of the medical image scanner device to facilitate reviewing whether the medical image series reflects one or more target characteristics for the performance of the 3D imaging scan while the patient is positioned relative to the medical image scanner device.

7. The system of claim 1, wherein the one or more characteristic detection algorithms comprise a series of detection algorithms applied to the one or more representative images, and wherein the scan characterization component selects subsequent detection algorithms in the series based on results of preceding detection algorithms in the series.

8. The system of claim 1, wherein the one or more characteristic detection algorithms comprise a first characteristic detection algorithm that determines the type of the medical image series based on the one or more representative images, and a second characteristic detection algorithm that determines a different characteristic of the medical image series based on the one or more representative images, wherein the scan characterization component selects the second characteristic detection algorithm from amongst a plurality of second characteristic detection algorithms based on the type of the medical image series, and wherein the second characteristic detection algorithms are respectively tailored to the different defined types.

9. The system of claim 8, wherein the second characteristic detection algorithm is selected from the group consisting of: a contrast phase detection algorithm, an anatomic region detection algorithm, and foreign object detection algorithm.

10. The system of claim 1, wherein the 3D to 2D image compression processes comprises:
selecting a sub-volume of the 3D image data; and
selecting the pixels from the 3D image data corresponding to the sub-volume, wherein the centroid comprises a centroid of the sub-volume.

11. The system of claim 1, wherein the different defined types correspond to different anatomical regions, and wherein respective scan images of each type of the different defined types depict a same anatomical region of the different anatomical regions.

12. The system of claim 1, wherein the medical image series comprises a computed tomography scan series or a magnetic resonance imaging scan series.

13. The system of claim 1, wherein the one or more representative images comprise at least two different representative images.

14. The system of claim 1, wherein the image generation component generates the one or more representative images from the 3D image data as at least one of, a multiplanar reconstruction (MRP) image with maximum intensity projection, or a MRP image with minimum intensity projection.

15. The system of claim 1, wherein the one or more characteristic detection algorithms comprise different series classification models respectively trained to classify the different defined types of medical image series in association with processing training images corresponding to the one or more representative images as generated from training 3D image data corresponding to the different types of the medical image series.

16. A method, comprising:
generating, by a system operatively coupled to a processor, one or more representative images of a medical image series comprising a plurality of scan images, wherein the medical image series is associated with three-dimensional (3D) image data representative of a 3D volume of an anatomical region of a patient, wherein each of the plurality of scan images correspond to different slices of the 3D volume, and wherein the generating comprises generating the one or more representative images from the 3D image data using a 3D to two-dimensional (2D) image compression processes that comprises generating a representative image of the one or more representative images using pixels included in the 3D image data and a weighting function for the pixels based on relative distances of the pixels to a centroid of the 3D image volume; and
applying, by the system, one or more characteristic detection algorithms to the one or more representative images to determine one or more characteristics of the medical image series, wherein the one or more characteristics comprise a type of the medical image series classified from amongst different defined types of medical image series.

17. The method of claim 16, further comprising:
generating, by the system, annotation metadata describing the one or more characteristics; and
associating, by the system, the annotation metadata with the image series as stored in one or more databases.

18. The method of claim 16, further comprising:
generating, by the system, a visualization layout for reviewing the medical image series via a medical imaging application based on the one or more characteristics, wherein the visualization layout varies for the different defined types; and
rendering, by the system, the medical image series according to the visualization layout in association with reviewing the medical image series via the medical imaging application.

19. The method of claim 16, further comprising:
selecting, by the system, one or more post-processing tasks for processing the medical image series based on the one or more characteristics; and
executing, by the system, the one or more post-post processing tasks based on the selecting.

20. The method of claim 16, wherein the one or more characteristic detection algorithms comprise a first characteristic detection algorithm that determines the type of the medical image series based on the one or more representative images, and a second characteristic detection algorithm that determines a different characteristic of the medical image series based on the one or more representative images, and wherein the method further comprises selecting, by the system, the second characteristic detection algorithm from amongst a plurality of second characteristic detection algorithms based on the type of the medical image series, wherein the second characteristic detection algorithms are respectively tailored to the different defined types, and wherein the second characteristic detection algorithm is selected from the group consisting of: a contrast phase detection algorithm, an anatomic region detection algorithm, and foreign object detection algorithm.

21. The method of claim 16, wherein the 3D to 2D image compression processes comprises:
selecting, by the system, a sub-volume of the 3D image data; and
selecting, by the system, pixels from the three-dimensional image data corresponding to the sub-volume wherein the centroid comprises a centroid of the sub-volume.

22. A non-transitory machine-readable storage medium, comprising executable instructions that, when executed by a processor, facilitate performance of operations, comprising:

generating one or more representative images of a medical image series comprising a plurality of scan images, wherein the medical image series is associated with three-dimensional (3D) image data representative of a 3D volume of an anatomical region of a patient, wherein each of the plurality of scan images correspond to different slices of the 3D volume, and wherein the generating comprises generating the one or more representative images from the 3D image data using a 3D to two-dimensional (2D) image compression processes that comprises generating a representative image of the one or more representative images using pixels included in the 3D image data and a weighting function for the pixels based on relative distances of the pixels to a centroid of the 3D image volume;

applying one or more characteristic detection algorithms to the one or more representative images to determine one or more characteristics of the medical image series, wherein the one or more characteristics comprise a type of the medical image series classified from amongst different defined types of medical image series; and performing one or more processing tasks related to the medical image series selected based on the one or more scan characteristics.

\* \* \* \* \*